US012791566B2

(12) United States Patent
Block et al.

(10) Patent No.: US 12,791,566 B2
(45) Date of Patent: Nov. 10, 2026

(54) TnT BASED DIAGNOSIS OF PAROXYSMAL ATRIAL FIBRILLATION

(71) Applicant: Roche Diagnostics Operations, Inc., Indianapolis, IN (US)

(72) Inventors: Dirk Block, Bichl (DE); Roberto Latini, Milan (IT); Serge Masson, Monza (IT); Ursula-Henrike Wienhues-Thelen, Krailling (DE); Christian Zaugg, Rheinfelden (DE); Andre Ziegler, Laeufelfingen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 17/821,951

(22) Filed: Aug. 24, 2022

(65) Prior Publication Data

US 2023/0062697 A1 Mar. 2, 2023

Related U.S. Application Data

(60) Division of application No. 15/359,674, filed on Nov. 23, 2016, now abandoned, which is a continuation of application No. 14/705,528, filed on May 6, 2015, now abandoned, which is a continuation of application No. PCT/EP2013/073476, filed on Nov. 11, 2013.

(30) Foreign Application Priority Data

Nov. 9, 2012 (EP) .................................... 12191996

(51) Int. Cl.

*G01N 33/53* (2006.01)
*G01N 33/68* (2006.01)
*G01N 33/74* (2006.01)

(52) U.S. Cl.

CPC ..... *G01N 33/6893* (2013.01); *G01N 33/6869* (2013.01); *G01N 33/6887* (2013.01); *G01N 33/74* (2013.01); *G01N 2333/4712* (2013.01); *G01N 2333/4737* (2013.01); *G01N 2333/4745* (2013.01); *G01N 2333/5412* (2013.01); *G01N 2333/58* (2013.01); *G01N 2800/326* (2013.01); *G01N 2800/52* (2013.01)

(58) Field of Classification Search

CPC ........... G01N 33/6893; G01N 33/6869; G01N 33/6887; G01N 33/53; G01N 33/543; G01N 2333/4712; G01N 2333/4737; G01N 33/4745; G01N 2333/58; G01N 2800/52

See application file for complete search history.

(56) References Cited

U.S. PATENT DOCUMENTS

| | | | |
|---|---|---|---|
| 5,744,305 A | 4/1998 | Fodor et al. | |
| 6,331,402 B1 | 12/2001 | Nussbaum et al. | |
| 6,709,855 B1 | 3/2004 | Stanton et al. | |
| 6,974,704 B2 | 12/2005 | Nelson et al. | |
| 8,354,235 B2 | 1/2013 | Bodenbach et al. | |
| 2003/0039584 A1 | 2/2003 | Schabbach et al. | |
| 2003/0232385 A1 | 12/2003 | Breit et al. | |
| 2006/0003338 A1 | 1/2006 | Deng et al. | |
| 2006/0110775 A1 | 5/2006 | Borgya et al. | |
| 2009/0176247 A1 | 7/2009 | Bashirians et al. | |
| 2009/0233312 A1 | 9/2009 | Gibbons et al. | |
| 2010/0197518 A1 | 8/2010 | Xu et al. | |
| 2010/0285491 A1 | 11/2010 | Wienhues-Thelen et al. | |
| 2011/0111524 A1 | 5/2011 | Goix et al. | |
| 2014/0220604 A1* | 8/2014 | Hess ................. | G01N 33/6887 435/7.92 |

FOREIGN PATENT DOCUMENTS

| | | |
|---|---|---|
| CN | 101107527 A | 1/2008 |
| CN | 101379401 A | 1/2008 |
| CN | 101393198 A | 3/2009 |
| CN | 101501067 A | 8/2009 |
| CN | 101506660 A | 8/2009 |
| EP | 0648228 A | 11/1998 |
| EP | 1577673 A1 | 9/2005 |
| EP | 2037278 A1 | 3/2009 |
| WO | 1999006445 A1 | 2/1999 |
| WO | 2000070051 A1 | 11/2000 |

(Continued)

OTHER PUBLICATIONS

Hammerer-Lercher et al., Analysis of Circulating Forms of proBNP and NT-proBNP in Patients with Severe Heart Failure, Clin. Chem., (2008), 54(5), p. 858-865 (Year: 2008).*

Van Den Bos et al., Minor elevations in troponin I are associated with mortality and adverse cardiac events in patients with atrial fibrillation, European Heart Journal, 2011, 32, pp. 611-617. (Year: 2011).*

Thacker et al., Atrial fibrillation and cognitive decline, Neurology, 81, Jul. 9, 2013, pp. 119-125 (Year: 2013).*

Noonan, Peggy; Study Finds Major Predictor for Development of New Atrail Fibrillation (AF), StopAfib..org, Nov. 16, 2009, pp. 1-3. (Year: 2009).*

Anegawa et al., High-sensitive troponin T is associated with atrial fibrillation in a general population, Int J Cardiol, 56 (1), pp. 98-100, available online Jan. 21, 2012 (Year: 2012).*

(Continued)

*Primary Examiner* — Gary Counts
(74) *Attorney, Agent, or Firm* — Taft Stettinius & Hollister LLP

(57) ABSTRACT

A method is disclosed herein for diagnosing a recent paroxysmal atrial fibrillation. The method is based on the determination of the at least one marker selected from the group consisting of a cardiac Troponin, NT-proBNP (N-terminal prohormone of brain natriuretic peptide), hsCRP, IL-6 (Interleukin-6) and IGFBP7 (Insulin like growth factor binding protein 7) in a sample from the subject, and on the comparison of the, thus, determined amount(s) with a reference amount (reference amounts). Further, the method can be used for identifying a subject being treatable with anticoagulation therapy. Further envisaged are systems, reagents and kits used in performing the methods disclosed herein.

11 Claims, No Drawings

(56) References Cited

FOREIGN PATENT DOCUMENTS

| | | | |
|---|---|---|---|
| WO | 2002083913 | A1 | 10/2002 |
| WO | 2002089657 | A1 | 11/2002 |
| WO | 2003016910 | A1 | 2/2003 |
| WO | 2003025571 | A1 | 3/2003 |
| WO | 2004059293 | A2 | 7/2004 |
| WO | 2005113585 | A2 | 12/2005 |
| WO | 2006087373 | A1 | 8/2006 |
| WO | 2006131529 | A1 | 12/2006 |
| WO | 2007090796 | A1 | 8/2007 |
| WO | 2007137865 | A1 | 12/2007 |
| WO | 2008015254 | A2 | 2/2008 |
| WO | 2008068780 | A2 | 6/2008 |
| WO | 2009047283 | A2 | 4/2009 |
| WO | 2009047285 | A1 | 4/2009 |
| WO | 2010007041 | A1 | 1/2010 |
| WO | 2010017972 | A1 | 2/2010 |
| WO | 2010046136 | A1 | 4/2010 |
| WO | 2010124821 | A1 | 11/2010 |
| WO | 2011012268 | A1 | 2/2011 |
| WO | 2012025355 | A1 | 3/2012 |
| WO | 2013057135 | A1 | 4/2013 |
| WO | 2014040459 | A1 | 3/2014 |
| WO | 2014072471 | A1 | 5/2014 |
| WO | 2014086833 | A1 | 6/2014 |

OTHER PUBLICATIONS

Goette et al., Acute atrial tachyarrhytmia induces angiotensin II type 1 receptor-mediated oxidative stress and micovascular flow abnormalities in the ventricles, European Heart Journal, 2009, pp. 1411-1420, vol. 30, No. 11.
Grigoryan et al., Impact of Inflammatory Markers on Pathogenesis and Clinical Outcomes at Different Types of Atrial Fibrillation, 2013, pp. 4-8, vol. 7, No. 3.
Gustafsson et al., Diagnostic and Prognostic Performance of N-Terminal ProBNP in Primary Care Patients With Suspected Heart Failure, Journal of Cardiac Failure, 2005, pp. S15-S20, vol. 11, No. 5, Supplement.
Heeringa et al., Prevalence, incidence and lifetime risk of atrial fibrillation: the Rotterdam study, European Heart Journal, 2006, pp. 949-953, vol. 27.
Hijazi et al., Troponin 1 elevation increases the risk of death and stroke in patients with atrial fibrillation, European Heart Journal, 2010, p. 886, vol. 31, Supplement 1.
Hijazi et al., Cardiac Biomarkers Are Associated With an Increased Risk of Stroke and Death in Patients With Atrial Fibrillation A Randomized Evaluation of Long-Term Anticoagulation Therapy (RE-LY) Substudy, Circulation, 2012, pp. 1605-1616, vol. 125.
Hromas et al., PLAB, a novel placental bone morphogenetic protein, Biochimica et Biophysica Acta, 1997, pp. 40-44, vol. 1354.
Hunt et al., ACC/AHA Guidelines for the Evaluation and Management of Chronic Heart Failure in the Adult: Executive Summary, Journal of the American College of Cardiology, 2001, pp. 2101-2113, vol. 38, No. 7.
Hunt et al., ACC/AHA 2005 Guideline Update for the Diagnosis and Management of Chronic Heart failure in the Adult, Journal of the American College of Cardiology, 2005, pp. e1-e82, vol. 46.
Hwa et al., The Insulin-Like Growth Factor-Binding Protein (IGFBP) Superfamily, Endocrine Reviews, 1999, pp. 761-787, vol. 20, No. 6.
International Search Report issued Mar. 3, 2014 in Application No. PCT/EP2013/073476, 8 pages.
Irby et al., Osteopontin regulates multiple functions contributing to human colon cancer development and progression, Clinical & Experimental Metastasis, 2004, pp. 515-523, vol. 21.
Jaffe et al., Biomarkers in Acute Cardiac Disease: The Present and the Future; State-Of-The-Art Paper, J. Am. Coll. Cardiol., 2006, vol. 48, pp. 1-11.
Jones et al.., Insulin-Like Growth Factors and Their Binding Proteins: Biological Actions, Endocrine Reviews, 1995, pp. 3-34, vol. 16, No. 1.
Juurlink et al., Rates of Hyperkalemia after Publication of the Randomized Aldactone Evaluation Study, The New England Journal of Medicine, 2004, pp. 543-551, vol. 351.
Kamel et al., Detection of Atrial Fibrillation and Secondary Stroke Prevention Using Telemetry and Ambulatory Cardiac Monitoring, Current Atherosclerosis Reports, 2011, pp. 338-343, vol. 13.
Karl et al., Development of a novel, N-Terminal-proBNP (NT-proBNP) assay with a low detection limit, Scandinavian Journal of Clinical & Laboratory Investigation Supplement, 1999, pp. 177-181, vol. 59, Supplement 230.
Ke et al., Calpain mediates cardiac troponin degradation and contractile dysfunction in atrial fibrillation, Journal of Molecular and Cellular Cardiology, 2008, pp. 685-693, vol. 45.
Kempf et al., Circulating Concentrations of Growth-Differentiation Factor 15 in Apparently Healthy Elderly individuals and Patients with Chronic Heart Failure as Assessed by a New Immunoradiometric Sandwich Assay, Clinical Chemistry, 2007, pp. 284-291, vol. 53, No. 2.
Kempf et al., Prognostic Utility of Growth Differentiation Factor-15 in Patients With Chronic Heart Failure, Journal of the American College of Cardiology, 2007, pp. 1054-1060, vol. 50, No. 11.
Kempf et al., The Transforming Growth Factor-β Superfamily Member Growth-Differentiation Factor-15 Protects the Heart From Ischemia/Reperfusion Injury, Circulation Research, 2006, pp. 351-360, vol. 98.
Kerr et al., Elevated Troponin after Stroke: A Systematic Review, Cerebrovascular Diseases, 2009, pp. 220-226, vol. 28.
Kirchhof et al., Comprehensive risk reduction in patients with atrial fibrillation: Emerging diagnostic and therapeutic options, Thrombosis and Haemostasis, 2011, pp. 1012-1019, vol. 106, No. 6.
Kirchhof et al., Comprehensive risk reduction in patients with atrial fibrillation: emerging diagnostic and therapeutic options—a report from the 3rd Atrial Fibrillation Competence NETwork/European Heart Rhythm Association consensus conference, Europace, 2012, pp. 8-27, vol. 14.
Klinkenberg et al., Diurnal Rhythm of Cardiac Troponin: Consequences for the Diagnosis of Acute Myocardial Infarction; Clin. Chem., 2016, vol. 62, pp. 1602-1611.
Kubo et al., Combined Measurements of Cardiac Troponin I and Brain Natriuretic Peptide Are Useful for Predicting Adverse Outcomes in Hypertrophic Cardiomyopathy, Circulation Journal, 2011, pp. 919-926, vol. 75.
Latini et al., Prognostic value of very low plasma concentrations of troponin T in patients with stable chronic heart failure; Circulation, 2007, vol. 116, pp. 1242-1249.
Latini et al., Circulating cardiovascular biomarkers in recurrent atrial fibrillation: data from the GISSI-Atrial Fibrillation Trial, Journal of Internal Medicine, 2011, pp. 160-171, vol. 269.
Lowbeer et al., Serum cardiac troponin T, troponin I, plasma BNP and left ventricular mass index in professional football players; J. Sci. Med. Sport, 2007, vol. 10, pp. 291-296.
Lawton et al., Identification of a novel member of the TGF-beta superfamily highly expressed in human placenta, Gene, 1997, pp. 17-26, vol. 203.
Li et al., B-type natriuretic peptide levels in patients with paroxysmal lone atrial fibrillation, Heart Vessels, 2006, pp. 137-140, vol. 21.
López-Bermejo et al., Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues, The Journal of Clinical Endocrinology & Metabolism, 2003, pp. 3401-3408, vol. 88, No. 7.
López-Bermejo et al., Insulin Resistance Is Associated With Increased Serum Concentration of IGF-Binding Protein-Related Protein 1 {IGFBP-rP1/MAC25), Diabetes, 2006, pp. 2333-2339, vol. 55.
Maglione et al., Two alternative mRNAs coding for the angiogenic factor, placenta growth factor (PIGF), are transcribed from a single gene of chromosome 14, Oncogene, 1993, pp. 2333-2339, vol. 8.
Marcus et al., Markers of Inflammation Before and Aller Curative Ablation of Atrial Flutter, Heart Rhythm, 2008, pp. 215-221, vol. 5, No. 2.

(56) References Cited

OTHER PUBLICATIONS

Masson et al., An Update on Cardiac Troponins as Circulating Biomarkers in Heart Failure, Current Heart Failure Reports, 2010, pp. 15-21, vol. 7.
Masson et al., Predicting atrial fibrillation recurrence with circulating inflammatory markers in patients in sinus rhythm at high risk for atrial fibrillation: data from the GISSI atrial fibrillation trial, Heart, 2010, pp. 1909-1914, vol. 96.
Maynard et al., Troponin T or troponin I as cardiac markers in ischaemic heart disease; Heart, 2000, vol. 83, pp. 371-373.
Mentz et al., Natriuretic Peptide-Guided Therapy for Heart Failure, 2011, pp. J031-J2037, vol. 75.
Mcclatchey, Clin. Lab. Medicine, 2002, Section 3, Part 14.
Morrish et al., Identification by Subtractive Hybridization of a Spectrum of Novel and Unexpected Genes Associated with In Vitro Differentiation of Human Cytotrophoblast Cells, Placenta, 1996, pp. 431-441, vol. 17.
Moses et al., Troponin I is present in human cartilage and inhibits angiogenesis, Proceedings of the National Academy of Sciences USA, 1999, pp. 2645-2650, vol. 96.
Mueller et al., Long-term stability of endogenous B-type natriuretic peptide (BNP) and amino terminal proBNP (NT-proBNP) in frozen plasma samples, Clinical Chemistry & Laboratory Medicine, 2004, pp. 942-944, vol. 12, No. 8.
Needleman et al., A General Method Applicable to the Search for Similarities in the amino Acid Sequence of Two Proteins, Journal of Molecular Biology, 1970, pp. 443-453, vol. 48.
Nolan et al., Suspension array technology: evolution of the flat-array paradigm, Trends in Biotechnology, 2002, pp. 9-12, vol. 20, No. 1.
O'Donoghue et al., Natriuretic peptides in heart failure: should therapy be guided by BNP levels?, Nature Reviews Cardiology, 2010, pp. 13-20, vol. 7.
O'Reilly et al., Endostatin: An Endogenous Inhibitor of Angiogenesis and Tumor Growth, Cell, 197, pp. 277-285, vol. 88, 1997.
Oh et al.., Synthesis and Characterization of Insulin-like Growth Factor-binding Protein (IGFBP)-7, The Journal of Biological Chemistry, 1996, pp. 30322-30325, vol. 271, No. 48.
Omland et al., A Sensitive Cardiac Troponin T Assay in Stable Coronary Artery Disease, The New England Journal of Medicine, 2009, pp. 2538-2547, vol. 361, No. 26.
Ortega et al., New functional roles for non-collagenous domains of basement membrane collagens, Journal of Cell Science, 2002, pp. 4201-4214, vol. 115.
Panteghini, Role and importance of biochemical markers in clinical cardiology; European Heart Journal, 2004, vol. 25, pp. 1187-1196.
Paralkar et al., Cloning and Characterization of a Novel Member of the Transforming Growth Factor-β/Bone Morphogenetic Protein Family, The Journal of Biological Chemistry, 1998, pp. 13760-13767, vol. 273, No. 22.
Patel et al., Rivaroxaban versus Warfarin in Nonvalvular Atrial Fibrillation, The New England Journal of Medicine, 2011, pp. 883-891, vol. 365, No. 10.
Patton et al., N-terminal pro-B-type natriuretic peptide is a major predictor of the development of atrial fibrillation: the Cardiovascular Health Study; Circulation, 2009, vol. 120, pp. 1768-1774.
Pearson et al., Markers of Inflammation and Cardiovascular Disease Application to Clinical and Public Health Practice A Statement for Healthcare Professionals From the Centers for Disease Control and Prevention and he American Heart Association, Circulation, 2003, pp. 499-511, vol. 107.
Pearson et al., Improved tools for biological sequence comparison, Proceedings of the National Academy of Sciences, 1988, pp. 2444-2448, vol. 85.
Petretto et al., Integrated genomic approaches implicate osteoglycin (Ogn) in the regulation of left ventricular mass, Nature Genetics, 2008, pp. 546-552, vol. 40, No. 5.
Rienstra et al., Symptoms and functional status of patients with atrial fibrillation: State of the art and future research opportunities; Circulation, 2012, vol. 125, pp. 2933-2943.
Rizos J Human Hypertension 2010 24 447 457, Hypertension and paroxysmal atrial fibrillation: a novel predictive role of high sensitivity C-reactive protein in cardioversion and long-term recurrence, Journal of Human Hypertension, 2010, pp. 447-457, vol. 24.
Rizos et al., Paroxysmal Atrial Fibrillation Is More Prevalent than Persistent Atrial Fibrillation in Acute Stroke and Transient Ischemic Attach Patients, 2011, pp. 276-282, vol. 32.
Rodriquez-Yanez et al., High serum levels of pro-brain natriuretic peptide (pro BNP) identify cardioembolic origin in undetermined stroke, Disease Markers, 2009, pp. 189-195, vol. 26.
Sadanaga et al., D-dimer levels positively correlate with B-type natriuretic peptide levels in patients with atrial fibrillation, International Journal of Cardiology, 2012, pp. 110-111.
Saenger et al., Multicenter analytical evaluation of a high-sensitivity troponin T assay; Clinica Chimica Acta, 2011, vol. 412, pp. 748-754.
Sata et al., C-reactive Protein and Atrial Fibrillation Is inflammation a consequence or a cause of atrial fibrillation?, Japanese Heart Journal, 2004, pp. 441-445, vol. 45.
Schaeffer et al., Complete structure of the human transferrin gene. Comparison with analogous chicken gene and human pseudogene, Gene, 1987, pp. 109-116, vol. 56.
Schou et al., Long-term clinical variation of NT-proBNP in stable chronic heart failure patients, European Heart Journal, 2007, pp. 177-182, vol. 28.
Schou et al., Unexplained week-to-week variation in BNP and NT-proBNP is low in chronic heart failure patients during steady state, European Journal of Heart Failure, 2007, pp. 68-74, vol. 9.
Shave et al., Exercise-Induced Cardiac Troponin Elevation: Evidence, Mechanisms, and Implications; State-Of-The-Art Paper, J. Am. Coll. Cardiol., 2010, vol. 56, pp. 169-176.
Shin et al., Plasma levels of NT-pro-BNP in patients with atrial fibrillation before and after electrical cardioversion, Z. Kardiol., 2005, vol. 94, pp. 795-800.
Smith et al., Comparison of Biosequences, Advances in Applied Mathematics, 1981, pp. 482-489, vol. 2.
Smith et al., Delayed metabolism of human brain natriuretic peptide reflects resistance to neutral endopeptidase, Journal of Endocrinology, 2000, pp. 239-246, vol. 167.
Song et al.,. Cardiac Troponin T Elevation After Stroke: Relationship Between Elevated Serum Troponin T, Stroke Location, and Prognosis, Journal of Clinical Neurology, 2008, pp. 75-83, vol. 4.
St. Croix et al., Genes Expressed In Human Tumor Endothelium, Science, 2000, pp. 1197-1202, vol. 289.
Sundstrom et al., Cardiac troponin-I and risk of heart failure: a community-based cohort study; European Heart Journal; 2009, vol. 30, pp. 773-781.
Tan et al., PTGF-β, a type β transforming growth factor (TGF-β) superfamily member, is a p53 target gene that inhibits tumor cell growth via TGF-β signaling pathway, Proceedings of the National Academy of Sciences, 2000, pp. 109-114, vol. 97, No. 1.
Tang et al., National Academy of Clinical Biochemistry Laboratory Medicine Practice Guidelines: Clinical Utilization of Cardiac Biomarker Testing in Heart Failure, Circulation, 2007, pp. e99-e109, vol. 116.
Tang et al., National Academy of Clinical Biochemistry Laboratory Medicine Practice Guidelines: Clinical Utilization of Cardiac Biomarker Testing in Heart Failure, Clinical Biochemistry, 2008, pp. 210-221, vol. 41.
Tasheva et al., Mimecan/osteoglycin-deficient mice have collagen fibril abnormalities, Molecular Vision, 2002, pp. 407-415, vol. 8.
Tate et al., The determination of the 99th centile level for troponin assays in an Australian reference population; Ann. Clin. Biochem., 2008, vol. 45, pp. 275-288.
Thygesen et al., Recommendations for the use of cardiac troponin measurement in acute cardiac care†; 2010, vol. 31, pp. 2197-2206.
Thygesen et al., How to use high-sensitivity cardiac troponins in acute cardiac care; European Heart Journal, 2012, vol. 33, pp. 2252-2257.
Torzewski et al., Animal Models of C-Reactive Protein, Mediators of Inflammation, 2014, 7 pages.

(56) References Cited

OTHER PUBLICATIONS

Trooyen et al.,. The use of cardiac troponin-1 to determine the incidence of myocardial injury in patients with acute stroke, Tidsskr Nor Laegefuren, 2001, pp. 421-425, vol. 121, No. 4, English abstract.
Tsuchida et al., Influence of Paroxysmal Atrial Fibrillation Attack on Brain Natriuretic Peptide Secretion, Journal of Cardiology, 2004, pp. 1-11, vol. 44, No. 1.
Ustrell et al., Cardiac Workup of Ischemic Stroke, Current Cardiology Reviews, 2010, pp. 175-183, vol. 6.
Van Den Bos et al., Minor elevations in troponin I are associated with mortality and adverse cardiac events in patients with atrial fibrillation, European Heart Journal, 2011, pp. 611-617, vol. 32.
Van Der Vekens et al., Human and equine cardiovascular endocrinology: beware to compare, Cardiovascular Endocrinology, 2013, pp. 67-76, vol. 2, No. 4.
Van Der Worp et al., Acute Ischemic Stroke, The New England Journal of Medicine, 2007, pp. 572-579, vol. 357.
Wachter et al., Natriuretic Peptides for the Detection of Paroxysmal Atrial Fibrillation in Patients with Cerebral Ischemia-the Find-AF Study, PLoS One, 2012, e34351, 7 pages., vol. 7, Issue 4.
Wallace et al., Prevalence and Determinants of Troponin T Elevation in the General Population, Circulation, 2006, pp. 1958-1965, vol. 113.
Williams et al., Use and Side-Effect Profile of Spironolactone in a Private Cardiologist's Practice, Clinical Cardiology, 2006, pp. 149-153, vol. 29.
Wu et al., Analytical and Clinical Evaluation of the Bayer ADVIA Centaur Automated B-Type Natriuretic Peptide Assay In Patients with Heart Failure: A Multisite Study, Clinical Chemistry, 2004, pp. 867-873, vol. 50, No. 5.
Yeh, CRP as a Mediator of Disease, Circulation, 2004, pp. 11-11-11-14, vol. 109 [suppl II].
Yeo et al., Multicenter evaluation of the Roche NT-proBNP assay and comparison to the Biosite Triage BNP assay, Clinica Chimica Acta, 2003, pp. 107-115, vol. 338.
Yokoyama-Kobayashi et al., Human cDNA Encoding a Novel TGF-βSuperfamily Protein Highly Expressed in Placenta, Journal of Biochemistry, 1997, pp. 622-626, vol. 122, No. 3.
Ülgen et al., The Relationship Between HSCRP Levels and P Wave Duration in Lone Paroxysmal Atrial Fibrillation Patients, International Journal of Cardiology, 2013, p. S22, vol. 163.
You et al., Antithrombotic therapy for atrial fibrillation: Antithrombotic Therapy and Prevention of Thrombosis, 9th ed: American College of Chest Physicians Evidence-Based Clinical Practice Guidelines; Chest, 2012, vol. 141, pp. e531S-e575S.
Zeller et al., High population prevalence of cardiac troponin I measured by a high-sensitivity assay and cardiovascular risk estimation: the MORGAM Biomarker Project Scottish Cohort; European Heart Journal; 2014, vol. 35, pp. 271-281.
Zweig et al., Receiver-Operating Characteristic {ROG) Plots: A Fundamental Evaluation Tool in Clinical Medicine, Clinical Chemistry, 1993, pp. 561-577, vol. 39, No. 4.
Xiong et al., Effects of paroxysmal atrial fibrillation on plasma levels of brain natriuretic peptide in the elderly patients with essential hypertension, Practical Geriatrics, 2007, pp. 42-44, vol. 21 No.1.
Xiong et al., Translation, 2007, 13-pages, PTO137062 Chinese article.
Xiong et al., Translation, 2007, 5-pages from Google Translate, Pract Geriatr, Feb. 2007, vol. 21, No. 1.
Opposition filed by Roche Diagnostics GmbH (Patentee in these proceedings) against EP2002260B1 in the name of Singulex, Inc., pp. 1, 4, and 30.
Abdollahi et al., Endoslalin's Antiangiogenic Signaling Network, Molecular Cell, 2004, pp. 649-663, vol. 13.
Adams et al., Classification of subtype of acute ischemic stroke. Definitions for use in a multicenter clinical trial. TOAST. Trial of Org 10172 in Acute Stroke Treatment., Stroke, 1993, pp. 35-41, vol. 24.
Adams et al., Guidelines for the Early Management of Adults With Ischemic Stroke, Stroke, 2007, pp. 1655-1711, vol. 38.
Agewall et al., Troponin elevation in coronary vs. non-coronary disease, European Heart Journal, 2011, pp. 104-411, vol. 32.
Alcaraz et al., Sample entropy of the main atrial wave predicts spontaneous termination of paroxysmal atrial fibrillation, Medical Engineering & Physics, 2009, pp. 917-922, vol. 31.
Alter et al., Non-Compaction cardiomyopathy in an adult with hereditary spherocytosis; The European Journal of Heart Failure, 2007, pp. 98-99, vol. 9.
Anderson et al., ACC/AHA 2007 Guidelines for the Management of Patients With Unstable Angina/Non-ST-Elevation Myocardial Infarction, Journal of the American College of Cardiology, 2007, pp. e1-e157, vol. 50, No. 7.
Anderson et al., Molecular Basis of Human Cardiac Troponin T Isoforms Expressed in the Developing, Adult, and Failing Heart, Circulation Research, 1995, pp. 681-686, vol. 76.
Apple et al., Plasma 99th Percentile Reference Limits for Cardiac Troponin and Creatine Kinase MZB Mass for Use with European Society of Cardiology/American College of Cardiology Consensus Recommendation; Proteomics and Protein Markers, Clinical Chemistry, 2003, vol. 49, No. 8.
Badran et al., Doppler-derived indexes and B-type natriuretic peptide in prediction of paroxysmal atrial fibrillation in, 2007.
Baek et al., Cyclooxygenase Inhibitors Regulate the Expression of a TGF-II Superfamily Member That Has Proapoptotic and Antitumorigenic Activities, Molecular Pharmacology, 2001, pp. 901-908, vol. 59, No. 4.
Beaulieu-Boire et al., Troponin Elevation Predicts Atrial Fibrillation in Patients with Stroke or Transient Ischemic Attach, Journal of Stroke and Cerebrovascular Diseases, 2013, pp. 978-983, vol. 22, No. 7.
Bauskin et al., The propeptide of macrophage inhibitory cytokine (MIC-1), a TGF-β superfamily member, acts as a quality control determinant for correctly folded MIC-1, The EMBO Journal, 2000, pp. 2212-2220, vol. 19, No. 10.
Beck-Da-Silva et al., Brain natriuretic peptide predicts successful cardioversion in patients with atrial fibrillation and maintenance of sinus rhythm, Canadian Journal of Cardiology, 2004, pp. 1245-1248, vol. 20, No. 12.
Becker, Biomarkers in Atrial Fibrillation: Investigating Biologic Plausibility, Cause, and Effect, Journal of Thrombosis and Thrombolysis, 2005, pp. 71-75, vol. 19, No. 1.
Boehm et al., Biomarkers: optimizing treatment guidance in heart failure, Clinical Research in Cardiology, 2011, pp. 973-981, vol. 100.
Bonow, New Insights Into the Cardiac Natriuretic Peptides, Circulation, 1996, pp. 1946-1950, vol. 93.
Bootcov et al., MIC-1, a novel macrophase inhibitory cytokine, is a divergent member of the TGF-β superfamily, Proceedings of the National Academy of Sciences USA, 1997, pp. 11514-11519, vol. 94.
Boriani et al., Improving Stroke Risk Stratification Using the CHADS2 and CHA2DS2-VASc Risk Scores in Patients With Paroxysmal Atrial Fibrillation by Continuous Arrhythmia Burden Monitoring; Stroke, 2011, vol. 42, No. 6, pp. 1768-1770.
Bottner et al., Characterization of the rat, mouse, and human genes of growth/differentiation factor-15/macrophage inhibiting cytokine-1 (GDF-15/MIC-1), Gene, 1999, pp. 105-111, vol. 237.
Brown, The predictive value of cardiac biomarkers in prognosis and risk stratification of patients with atrial fibrillation, Current Opinion in Cardiology, 2011, pp. 449-456, vol. 26.
Burnicourat et al., Troponin Levels Help Predict New-Onset Atrial Fibrillation in Ischaemic Stroke Patients: A Retrospective Study, European Neurology, 2009, pp. 24-28, vol. 63.
Cadamuro et al., Cardiac Troponins T and I: Reproducible Discrepancies in the Clinical Setting; Clin. Chem., 2011, vol. 57, pp. 134-140.
Cai et al., The role of cardiac troponin I in prognostication of patients with isolated severe traumatic brain injury; J. Trauma Acute Care Surg., 2016, vol. 80, pp. 477-483.
Cairns et al., Canadian Cardiovascular Society Atrial Fibrillation Guidelines 2010: Prevention of Stroke and Systemic Thromboem-

(56) References Cited

OTHER PUBLICATIONS bolism in Atrial Fibrillation and Flutter, Canadian Journal of Cardiology, 2011, pp. 74-90, vol. 27.
Camm et al., The Task Force for the Management of Atrial Fibrillation of the European Society of Cardiology ESC), European Heart Journal, 2010, vol. 31, pp. 2369-2429.
Cheng et al., Correlation between atrial fibrillation, serum amyloid protein A and other inflammatory cytokines, Molecular Medicine Reports, 2012, pp. 581-584, vol. 6.
Choudhury et al., Soluble CD40 Ligand, Platelet Surface CD40 Ligand, and Total Platelet CD40 Ligand in Atrial Fibrillation, Chest, 2008, pp. 574-581, vol. 134.
Cohen et al., D-dimers in atrial fibrillation: a further step in risk stratification of thrombo-embolism?, European Heart Journal, 2007, pp. 2179-2180, vol. 28.
Conrad et al., Cardiac Troponins and High-sensitivity Cardiac Troponin Assays; Clin. Lab. Med, 2014, vol. 34, pp. 59-73.
Di Angelantonio et al., Prognostic significance of admission levels of troponin I in patients with acute ischaemi stroke, Journal of Neurology, Neurosurgery & Psychiatry, 2005, pp. 76-81, vol. 76.
De Filippi et al., Clinical Validation of a Novel Assay for Galectin-3 for Risk Assessment in Acutely Destabilized Heart Failure, The 13th Annual Scientific Meeting HFSA, 2009, p. S9, Abstract 020.
Dickstein et al., ESC Guidelines for the diagnosis and treatment of acute and chronic heart failure 2008, European Heart Journal, 2008, pp. 2388-2442, vol. 29.
Dieplinger et al., Long-term stability of soluble ST2 in frozen plasma samples, Clinical Biochemistry, 2010, pp. 1169-1170, vol. 43.
Donnan et al., Stroke, The Lancet, 2008, pp. 1612-1623, vol. 371, Issue 9324.
Dou et al., Nephrotoxic effect of melamine-contaminated fodder on rat: a metabonomic study, Chinese Journal of Pharmacology & Toxicology, 2011, pp. 88-92, vol. 25, No. 1.
Ellinor et al., Discordant atrial natriuretic peptide and brain natriuretic peptide levels in lone atrial Fibrillation, JACC, 2005.
Etgen et al., Cardiac Troponins and N-Terminal Pro-Brain Nalriurelic Peptide in Acute Ichemic Stroke Do Nol Relate to Clinical Prognosis, Stroke, 2005, pp. 270-275, vol. 36.
Fan et al., NT-proBNP, but not ANP and C-reactive protein, is predictive of paroxysmal atrial fibrillation in patients undergoing pulmonary vein isolation, Interv. Card Electrophysiol., Jan. 23, 2012, vol. 33, No. 1, pp. 93-100.
Federico, Natriuretic Peptide System and Cardiovascular Disease; Heart Views, 2010, vol. 11, pp. 10-15.
Ferrieres et al., Human cardiac troponin I: precise identification of antigenic epitopes and prediction of secondary structure, Clinical Chemistry, 1998, pp. 487-493, vol. 44, No. 3.
Finsterer et al., Positive troponin-T in noncompaction is associated with neuromuscular disorders and poor outcome, Clinical Research in Cardiology, 2007, pp. 109-113, vol. 96.
Fonarow et al., Usefulness of B-Type Natriuretic Peptide and Cardiac Troponin Levels to Predict In-Hospital Mortality from ADHERE, American Journal of Cardiology, 2008, pp. 231-237, vol. 101.
Foreman et al., Cardiac Troponin-1 Plasma Concentration in Normal Horses and in Horses with Arrhythmias and Toxicities, ACVIM Abstracts, 2005, p. 478, Abstract No. 286.
Fure et al., Electrocardiogramd troponin T changes in acute ischaemic stroke, Journal of Internal Medicine, J006, pp. 592-597, vol. 259, 2006.
Fuster et al., ACC/AHA/ESC Guidelines for the Management of Patients With Atrial Fibrillation: Executive Summary, Circulation, 2001, pp. 2118-2150, vol. 104.
Gahlmann et al., Differential expression of slow and fast skeletal muscle troponin C: Slow skeletal muscle troponin C is expressed in human fibroblasts; J. Mol. Biol., 1988, vol. 201, pp. 379-391.
Garcia-Berrocosco et al., Blood Biomarkers in Cardioembolic Stroke, Current Cardiology Reviews, 2010, pp. 194-201, vol. 6.
Gardner et al., N-terminal pro-brain natriuretic peptide A new gold standard in predicting mortality in patients with advanced heart failure, European Heart Journal, 2003, pp. 1735-1743, vol. 24.
Goei et al., Influence of Renal Function on the Usefulness of N-Terminal Pro-B-Type Natriuretic Peptide as a Prognostic Cardiac Risk Marker in Patients Undergoing Noncardiac Vascular Surgery, American Journal of Cardiology, 2008, pp. 122-126, vol. 101.
Markus, "An introduction to stroke", Stroke Genetics, Oxford University Press, Incorporated, 2003.
Written Opinion of the International Searching Authority, European Patent Office, International Patent Application No. PCT/EP2013/073476, May 15, 2014, 12 pages.
International Preliminary Report on Patentability, European Patent Office, International Patent Application No. PCT/PCT/EP2013/073476, May 12, 2015, 13 pages.
Akaogi et al., Specific accumulation of tumor-derived adhesion factor in tumor blood vessels and in capillary tube-like structures of cultured vascular endothelial cells, Proc Natl Acad Sci USA, vol. 93, 1996, pp. 8384-8389.
Burger et al., Down-regulation of T1A12/mac25, a novel insulin-like growth factor binding protein related gene, is associated with disease progression in breast carcinomas, Oncogene, vol. 16, 1998, pp. 2459-2467.
Dowdy et al., "Statistics for Research", 1983, John Wiley & Sons.
Ono et al., Expression of prostacyclin-stimulating factor, a novel protein, in tissues of Wistar rats and in cultured cells, Biochem Biophys Res Comm, vol. 202, 1994, pp. 1490-1496.
Woo et al., Characterization of Genomic and Complementary DNA Sequence of Human C-reactive Protein, and Comparison with the Complementary DNA Sequence of Serum Amyloid P Component*, J. Biol. Chem., vol. 260, No. 24, 1985, pp. 13384-13388.
Levey et al., A More Accurate Method To Estimate Glomerular Filtration Rate from Serum Creatinine: A New Prediction Equation, Annals of Internal Medicine, 1999.
Sprenger et al., Insulin-like Growth Factor Binding Protein-related Protein 1 (IGFBP-rP1) Is a Potential Tumor Suppressor Protein for Prostate Cancer1, C.C et al., Cancer Res, vol. 59, 1999.

* cited by examiner

TnT BASED DIAGNOSIS OF PAROXYSMAL ATRIAL FIBRILLATION

CROSS-REFERENCE TO RELATED APPLICATIONS

This application is a divisional application of U.S. application Ser. No. 15/359,674 filed Nov. 23, 2016, now abandoned, which is a continuation of U.S. application Ser. No. 14/705,528 filed May 6, 2015, now abandoned, which is a continuation of International Application No. PCT/EP2013/073476 filed Nov. 11, 2013, which claims priority to Application No. EP 12191996.3 filed Nov. 9, 2012, the disclosures of which are hereby incorporated by reference in their entirety.

BACKGROUND OF THE INVENTION

Atrial fibrillation is the most common cardiac arrhythmia. However, atrial fibrillation (AF) is frequently no recognized by the patient. This is the case in approximately 40% of patients indicating that history taking in insensitive for the diagnosis of atrial fibrillation (Kamel H. et al, Curr Atheroscler Rep 2011:13: 338-343). While these numbers relate to persistent atrial fibrillation, paroxysmal atrial fibrillation is even more difficult to diagnose and can only be captured by inpatient cardiac telemetry or even Holter Monitoring. Thus recognition of paroxysmal atrial fibrillation is a significant challenge, specifically as at least 1% of the general population has persistent atrial fibrillation and the frequency increases with age (Rizos T. et al).

Paroxysmal atrial fibrillation is defined as recurrent episodes of atrial fibrillation that terminate spontaneously in less than seven days, usually less than 24 hours. It may be either self-terminating or intermittent. Paroxysmal atrial fibrillation is common (5-10% of elderly subjects (see Prevalence, incidence and lifetime risk of atrial fibrillation: the Rotterdam study. Heeringa et al., Eur Heart J. 2006; 27 (8): 949). Untreated patients have an increased stroke risk (w/o anticoagulation).

The Gold Standard to detect atrial fibrillation is the electrocardiogram (ECG), preferably performed as 24 hour ECG (Holter Monitoring). However, Holter Monitoring can only detect atrial fibrillation if the arrhythmia occurs in the 24 hour period of ECG recording.

Several publications implicate the association of biomarkers at enhanced levels with atrial fibrillation (Biomarkers in Atrial Fibrillation: Investigating Biologic Plausibility, Cause, and Effect R. Becker Journal of Thrombosis and Thrombolysis 19 (1), 71-75, 2005).

Nt-ProBNP assessment provides a means to assess systolic dysfunction. High sensitive Troponin assays allow the detection of subclinical cardiac injury. It has been described, that elevated levels of both, Troponin T and Nt-ProBNP independently predict a higher risk of a first recurrence of atrial fibrillation after 6 or 12 months (Circulating cardiovascular biomarkers in recurrent atrial fibrillation: data from the GISSI-Atrial Fibrillation Trial, R. Latini et al., J Intern Med2011; 269:160-171). I. Beaulieu-Boire described elevated cTnI levels in patients with acute ischemic stroke (AIS) or transient ischemic attack (TIA) is predictive of new-onset AF and associated with a poorer prognosis and higher mortality rate (I. Beaulieu-Boire et. al. J Stroke Cerebrovasc Dis. 2012 Feb. 15, available online, in press).

Several other publications describe the association of increased levels of biomarkers with the diagnosis and/or prediction of atrial fibrillation (Kirchhof et al., 2011 Jul. 26, Europace Epub, Comprehensive risk reduction in patients with atrial fibrillation: emerging diagnostic and therapeutic options—a report from the 3rd Atrial Fibrillation Competence NETwork/European Heart Rhythm Association consensus conference; Circulating cardiovascular biomarkers in recurrent atrial fibrillation: data from the GISSI-Atrial Fibrillation Trial, R. Latini et al., J Intern Med 2011; 269:160-171). Blood biomarkers which would allow for diagnosing the recent occurrence of paroxysmal atrial fibrillation are highly desired since the determination of these biomarkers would allow for identifying patients which may benefit from anticoagulation therapy.

Bugnicourt et al. 2010 (Eur Neurol 2010; 63:24-28) discloses that cardiac troponin I levels predict new-onset atrial fibrillation in ischaemic stroke patients. It also disclosed that elevated troponin I levels are known to be associated with atrial fibrillation.

Hijazi et al. 2012 (Circulation. 125:1605-1616) discloses that elevations of troponin I and NTproBNP are common in patients with AF and independently related to increased risks of stroke and mortality.

Marcus et al. 2008 (Heart Rhythm. 2008 February; 5 (2): 215-21) discloses that CRP and IL-6 levels are elevated in patients presenting with atrial fibrillation.

Choudhury et al. 2008 (September; 134 (3): 574-81) discloses a sCD40L detection based method of diagnosing atrial fibrillation. Specifically, AF patients had significantly higher sCD40L levels compared to healthy control subjects.

Cohen et al. 2007 (doi: 10.1093/eurheartj/ehm170) reports on a D-dimer detection based method of diagnosing atrial fibrillation.

Latini et al. 2011 (J Intern Med. 2011 February; 269 (2): 160-71) discloses a method for predicting reoccurance of atrial fibrillation based on the detection of NTproANP, hsTnT or NTproBNP in patients with a history of AF.

Wachter et al. 2012 (PLOS ONE 7 (4): e34351. doi: 10.1371/journal.pone.0034351) discloses that BNP may be used to detect paroxysmal AF.

Rizos et al. 2010 (Journal of Human Hypertension 24, 447-457) discloses that hsCRP and IL-6 may be used to detect paroxysmal AF.

The technical problem underlying the present invention can be seen as the provision of means and methods for complying with the aforementioned needs.

SUMMARY OF THE INVENTION

The present invention relates to a method for diagnosing a recent paroxysmal atrial fibrillation. The method is based on the determination of the at least one marker selected from the group consisting of a cardiac Troponin, NT-proBNP (N-terminal prohormone of brain natriuretic peptide), hsCRP, IL-6 (Interleukin-6) and IGFBP7 (Insulin like growth factor binding protein 7) in a sample from the subject, and on the comparison of the, thus, determined amount(s) with a reference amount (reference amounts). Further, the present invention relates to a method for identifying a subject being treatable with anticoagulation therapy and to a method for diagnosing an ongoing atrial fibrillation based on the determination of the amount of IGFBP7. Further envisaged are systems, reagents and kits used in performing the methods disclosed herein.

DETAILED DESCRIPTION OF THE INVENTION

The technical problem is solved by the embodiments characterized in the claims and herein below.

Accordingly, the present invention relates to a method for diagnosing a recent paroxysmal atrial fibrillation in a subject, comprising:

(a) determining the amount of at least one marker selected from the group consisting of a cardiac Troponin, a BNP-type peptide, in particular NT-proBNP (N-terminal prohormone of brain natriuretic peptide), hsCRP, IL-6 (Interleukin-6) and IGFBP7 (Insulin like growth factor binding protein 7) in a sample from the subject, and (b) comparing the, thus, determined amount(s) of said at least one marker to a reference amount (to reference amounts), whereby a recent paroxysmal atrial fibrillation is diagnosed, wherein the subject does not suffer from atrial fibrillation at the time at which the sample is obtained.

Preferably, a recent paroxysmal atrial fibrillation is diagnosed by carrying out the further step of c) diagnosing a recent paroxysmal fibrillation, based on the results of the comparison carried out in step b).

In an embodiment, the determination of the amount(s) of the biomarker(s) in step (a) is done by contacting the sample with a detection agent that specifically binds to the biomarker (or with detection agents that specifically bind to the biomarkers), thereby forming an complex with the detection agent and the biomarker, detecting the amount(s) of the complex(es) formed, thereby determining the amount of the biomarker. The term "detection agent" has been specified elsewhere herein.

In an embodiment, the aforementioned method may further comprise the step (c) of providing a diagnosis of recent paroxysmal atrial fibrillation when the amount of the biomarker(s) in the sample from the subject is above the reference amount(s) and/or of providing a diagnosis of the absence of atrial fibrillation when the amount(s) of the biomarker(s) in the sample from the subject is below the reference amount.

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison and/or assessment based on said comparison in step (b).

Accordingly, the present invention also preferably relates to a system for diagnosing a recent paroxysmal atrial fibrillation in a subject, comprising a) an analyzer unit configured to contact, in vitro, a portion of a sample from a subject suffering from pneumonia with a ligand (or ligands) comprising specific binding affinity for at least one marker selected from the group consisting of a cardiac Troponin, a BNP-type peptide, hsCRP (high sensitive CRP), IL-6 (Interleukin-6) and IGFBP7 (Insulin like growth factor binding protein 7), b) an analyzer unit configured to detect a signal from the portion of the sample from the subject contacted with the ligand (or ligands), c) a computing device having a processor and in operable communication with said analysis units, and d) a non-transient machine readable media including a plurality of instruction executable by a the processor, the instructions, when executed calculate an amount (or amounts) of the at least one marker, and compare the amount (or amounts) of the at least one marker with a reference amount (or with reference amounts), thereby diagnosing a recent paroxysmal atrial fibrillation in the subject.

The term "diagnosing" as used herein, preferably, means assessing whether a subject as referred to herein has recently suffered from a paroxysmal atrial fibrillation, or not. In particular, it is assessed whether the subject has recently suffered from an episode of paroxysmal atrial fibrillation, or not. As will be understood by those skilled in the art, such an assessment is usually not intended to be correct for 100% of the subjects to be diagnosed. The term, however, requires that the assessment is correct for a statistically significant portion of the subjects (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc., Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

In the context of the present invention, a recent paroxysmal atrial fibrillation shall be diagnosed, i.e. it shall be diagnosed whether the subject has recently suffered from paroxysmal atrial fibrillation, or not.

The term "atrial fibrillation" is well known in the art. Atrial fibrillation is e.g. reviewed by Fuster et al. which herewith is incorporated by reference in its entire disclosure content (Fuster V, Rydén L E, Asinger R W, et al. ACC/AHA/ESC Guidelines for the Management of Patients With Atrial Fibrillation: Executive Summary A Report of the American College of Cardiology/American Heart Association Task Force on Practice Guidelines and the European Society of Cardiology Committee for Practice Guidelines and Policy Conferences (Committee to Develop Guidelines for the Management of Patients With Atrial Fibrillation) Developed in Collaboration With the North American Society of Pacing and Electrophysiology. Circulation. Oct. 23 2001; 104 (17): 2118-50). Atrial fibrillation is an abnormal heart rhythm which involves the two upper chambers of the heart. In a normal heart rhythm, the impulse generated by the sino-atrial node spreads through the heart and causes contraction of the heart muscle and pumping of blood. In atrial fibrillation, the regular electrical impulses of the sino-atrial node are replaced by disorganized, rapid electrical impulses which result in irregular heart beats.

Atrial fibrillation (AF) can be permanent, persistent or paroxysmal (frequently also referred to as "intermittent").

A subject, preferably, suffers from permanent AF, if the AF has persisted for more than one year. In particular, conversion back to sinus rhythm does not occur (or only if treated).

A subject, preferably, suffers from persistent AF, if the AF lasts more than 7 days and may require either pharmacologic or electrical intervention to terminate atrial fibrillation. Thus persistent AF occurs in episodes, but the arrhythmia does not convert back to sinus rhythm spontaneously.

In the context of the present invention, a recent paroxysmal atrial fibrillation shall be diagnosed, in particular an episode of paroxysmal atrial fibrillation that occurred recently (before the sample has been obtained). Paroxysmal atrial fibrillation, preferably, refers to an intermittent episode of atrial fibrillation lasting minutes up to seven days. Preferably, the episode last less than one hour. More preferably, the episode lasts less than one day. Even more, preferably, the episode lasts less three days or five days. Preferably, the episode of atrial fibrillation did terminate spontaneously. Accordingly, the atrial fibrillation, preferably, terminated spontaneously.

The term "spontaneous" in connection with the termination of atrial fibrillation is well understood by the skilled person. The term "spontaneous termination" as used herein, preferably, means that atrial termination terminated without intervention, in particular without cardioversion.

Preferably, a paroxysmal atrial fibrillation is deemed to have occurred recently, if it occurred up to twelve weeks before carrying out the method of the present invention (or, to be more precise, if it occurred up to twelve weeks before the sample to be tested has been obtained). Accordingly, it is diagnosed whether the subject has suffered from paroxysmal atrial fibrillation (or not), in particular an episode of paroxysmal atrial fibrillation within a period of twelve weeks before the sample has been obtained.

More preferably, a paroxysmal atrial fibrillation is deemed to have occurred recently, if it occurred up to six weeks before the sample has been obtained. Accordingly, it is diagnosed whether the subject has suffered from paroxysmal atrial fibrillation (or not), in particular an episode of paroxysmal atrial fibrillation within a period of six weeks before the sample has been obtained.

Even more preferably, a paroxysmal atrial fibrillation is deemed to have occurred recently, if it occurred up to 15 or 30 days before the sample has been obtained. Accordingly, it is diagnosed whether the subject has suffered from paroxysmal atrial fibrillation (or not), in particular an episode of paroxysmal atrial fibrillation, within a period of 15 or 30 days (in particular 30 days) before the sample has been obtained. In an embodiment the recent paroxysmal AF occurred within 1 to 30 days before the sample has been obtained.

Even more preferably, a paroxysmal atrial fibrillation is deemed to have occurred recently, if it occurred up to seven days before the sample has been obtained. Accordingly, it is diagnosed whether the subject has suffered from paroxysmal atrial fibrillation (or not), in particular an episode of paroxysmal atrial fibrillation, within a period of one week before the sample has been obtained. In particular, it is preferred that the recent paroxysmal atrial fibrillation occurred within 1 to 7 days before the sample has been obtained.

Also, it is envisaged that the recent paroxysmal atrial fibrillation occurred within 72 hours before the sample has been obtained.

Preferably, the periods referred to herein are drawn to the termination of the last episode of atrial fibrillation.

The term "subject" as used herein relates to animals, preferably mammals, and, more preferably, humans. The subject may be male (in particular a male being older than 60 or 65 years). Further, the subject may be female (in particular a female being older than 60 or 65 years). Moreover, it is envisaged that the subject does not suffer from atrial fibrillation, in particular does not suffer from atrial fibrillation, i.e. does not exhibit an episode of AF, at the time at which the sample to be tested has been obtained. Whether a subject suffer from atrial fibrillation at this time, or not, can be determined by the skilled person without further ado. Preferably, a subject who does not suffer from atrial fibrillation shows a normal sinus rhythm of the heart (or vice versa: a subject who does not suffer from atrial fibrillation does not show an abnormal sinus rhythm). Thus, if the subject suffers from a recent paroxysmal atrial fibrillation, the atrial fibrillation shall have converted back to (normal) sinus rhythm, in particular, at the time at which the sample has been obtained. Preferably, the atrial fibrillation shall have converted back to (normal) sinus rhythm at least 30 minutes before the sample has been obtained. Accordingly, the subject shall not have exhibited an episode of atrial fibrillation (AF) within 30 minutes before the sample has been obtained. Preferably, the atrial fibrillation shall have converted back to (normal) sinus rhythm at least 3 or 6 hours before the sample has been obtained. More preferably, the atrial fibrillation shall have converted back to (normal) sinus rhythm at least 24 or 36 hours before the sample has been obtained. Even more preferably, the atrial fibrillation shall have converted back to (normal) sinus rhythm at least 72 hours before the sample has been obtained. Also envisaged is that the atrial fibrillation shall have converted back to (normal) sinus rhythm at least 6 days before the sample has been obtained.

Accordingly, the subject, preferably, shall not have exhibited an episode of atrial fibrillation (AF) within 30 minutes before the sample has been obtained. Also preferably, the subject shall not have exhibited an episode of atrial fibrillation (AF) within 3 or 6 hours before the sample has been obtained. More preferably, the subject shall not have exhibited an episode of atrial fibrillation (AF) within 24 or 36 hours before the sample has been obtained. Even more preferably, the subject did not exhibit an episode of atrial fibrillation (AF) within 72 hours before the sample has been obtained. Also envisaged is that the subject did not exhibit an episode of atrial fibrillation (AF) within 6 days before the sample has been obtained. Accordingly, it is envisaged that the recent paroxysmal AF to be diagnosed did not occur within the aforementioned periods. Preferably, the periods mentioned above are drawn to the termination of the (last) episode of paroxysmal AF.

In accordance with the present invention it is, thus, envisaged to diagnose paroxysmal AF, in particular an episode of paroxysmal AF, that occurred (in particular that terminated) preferably, more than 30 minutes, more preferably, more than 3 or 6 hours, even more preferably, more than 24 or 36 hours, and, most preferably, more than 72 hours before the sample has been obtained, but, preferably, less than 7 days, more preferably, less than 15 days, and, most preferably, less than 30 days before the sample has been obtained.

In preferred embodiment, it is envisaged to diagnose paroxysmal AF, in particular an episode of paroxysmal AF, that occurred (in particular that terminated) more than 30 minutes or 3 hours, but less than 7 days before the sample has been obtained. In another embodiment, it is envisaged to diagnose paroxysmal AF, in particular an episode of paroxysmal AF, that occurred (in particular that terminated) more than 6 hours but less than 7 days before the sample has been obtained. In another embodiment, it is envisaged to diagnose paroxysmal AF, in particular an episode of paroxysmal AF, that occurred (in particular that terminated) more than 24 hours but less than 15 or 30 days before the sample has been obtained. Also, it is envisaged to diagnose paroxysmal AF, in particular an episode of paroxysmal AF, that occurred (in particular that terminated) more than 72 hours but less than 30 days before the sample has been obtained.

Further, it is envisaged to diagnose paroxysmal AF, in particular an episode of paroxysmal AF, that occurred (in particular that terminated) more than 6 hours but less than 72 hours before the sample has been obtained.

Preferably, the periods mentioned above are drawn to the termination of the (last) episode of paroxysmal AF.

The subject in accordance with the aforementioned method of the present invention shall be suspected to have suffered from a recent paroxysmal atrial fibrillation. A subject suspected to have suffered from a recent atrial fibrillation, preferably, is a subject who has one or more risk factors of atrial fibrillation. These risk factors are well known in the art and include heart disease, including valve problems and a history of heart attack and heart surgery, systemic hypertension, especially if it's not well controlled with lifestyle changes or medications, and alcohol consumption. Preferably, the subject being suspected to belongs to a risk group. In particular, it is envisaged that the subject is a subject with proven or suspected cardiac disorders including subjects having risk factors predisposing to cardiac disorders such as arterial or systemic hypertension, diabetes mellitus, smokers, individuals with hyperlipemia or signs of the metabolic syndrome, in particular if the subject is at advanced age (more than 60, 65, 70 and preferably more than 75, or 80 years of age). Alternatively, or additionally the subject may, preferably, suffer from valvular disorders, preferably from mitral valve disorders.

In a particular preferred embodiment of the method of the present invention the subject suffers from hypertension and/or from heart failure.

In an embodiment of the present invention, the subject is not a 58 years old male.

The hypertension can be any form of hypertension known to the person skilled in the art. In a preferred embodiment of the present invention, the individual suffers from arterial hypertension, systolic and/and or diastolic hypertension. In particular, the subject shall suffer from arterial hypertension. Preferably, a subject suffers from arterial hypertension, if systolic pressure exceeds 140 mmHg and/or the diastolic pressure exceeds 90 mmHg. More preferably, a subject suffers from arterial hypertension, if systolic pressure exceeds 140 mmHg and/or the diastolic pressure exceeds 90 mmHg for three months or more, six months or more, twelve months or more, two years or more, three years or more, or five years or more.

The term "heart failure" as used herein, preferably, relates to an impaired systolic and/or diastolic function of the heart being accompanied by overt signs of heart failure as known to the person skilled in the art. Preferably, heart failure referred to herein is also chronic heart failure. Heart failure according to the present invention includes overt and/or advanced heart failure. In overt heart failure, the subject shows symptoms of heart failure as known to the person skilled in the art. It is particularly contemplated that the term "heart failure" as used herein refers to stages C and D of the ACC/AHA classification. In these stages, the subject shows typical symptoms of heart failure, i.e. the subject is not apparently healthy. The subject having heart failure and being classified into stage C or D has undergone permanent, non reversible structural and/or functional changes to his myocardium, and as a consequence of these changes, full health restoration is not possible.

The ACC/AHA classification is a classification for heart failure developed by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF (heart failure) but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy (LVH, a phenomenon in which the walls of the ventricles thicken) and/or impaired LV function would be designated as stage B. Stage C then denotes patients with current or past symptoms of HF associated with underlying structural heart disease (the bulk of patients with HF), and stage D designates patients with truly refractory HF.

In a preferred embodiment of the present invention, the subject to be tested is classified as stage A subject (according to the ACC/AHA classification as referred to above).

Preferably, the recent paroxysmal atrial fibrillation to be diagnosed did not occur in connection with stroke. In particular, it is envisaged that the subject shall not have not have a history of stroke.

Preferably, paroxysmal atrial fibrillation is deemed to have been occurred in connection with stroke if there is a temporal and/or causal relationship between the paroxysmal atrial fibrillation and stroke. Preferably, paroxysmal atrial fibrillation is deemed to have been occurred in connection with stroke, if it occurred within one week prior and/or after a stroke. More preferably, paroxysmal atrial fibrillation is deemed to have been occurred in connection with stroke, if it occurred within one month prior and/or after a stroke.

Preferably, a subject who has no history of stroke did not suffer from stroke within three months before the sample to be tested has been obtained. More preferably, a subject who has no history of stroke did not suffer from stroke at all before the sample to be tested has been obtained.

The term "stroke" is well known in the art. As used herein, the term, preferably, refers to the sudden death of cells in a specific area of the brain due to disruption of blood flow to the brain. Stroke may also be referred to as cerebral accident, cerebral infarction, or cerebrovascular accident. Disruption of blood flow to the brain may be caused by blockage of an artery or an artery bursting, preventing normal blood circulation. A stroke may be preceded by transient ischemic attacks (TIAs), or a mini-stroke, which are characterized by temporarily disrupted blood flow to the brain. A stroke can lead to loss of vision, loss of speech, loss of muscular control, loss of consciousness, coma and death.

It is particularly, envisaged that the recent paroxysmal atrial fibrillation did not occur in connection with ischemic stroke. The term "ischemic stroke" (herein also referred to as "stroke") is well known by the skilled person (see e.g. Adams et al., Guidelines for the Early Management of Adults With Ischemic Stroke, A Guideline From the American Heart Association/American Stroke Association Stroke Council, Clinical Cardiology Council, Cardiovascular Radiology and Intervention Council, and the Atherosclerotic Peripheral Vascular Disease and Quality of Care Outcomes in Research Interdisciplinary Working Groups in Stroke. 2007; 38:1655; or Stroke Genetics, edited by Hugh S. Markus, Chapter 1 "An introduction to stroke, Oxford University Press, Incorporated, Publish Date 06/03, both of which are herewith incorporated by reference with respect to its entire disclosure content). As used herein, the term, preferably, refers to cerebral ischemic stroke. Ischemic stroke is caused by reduced blood flow to the brain or parts thereof which leads to a reduced delivery (undersupply) of oxygen to brain cells. Ischemic stroke may be characterized by tissue anemia caused by obstruction of the inflow of arterial blood. It may lead to irreversible tissue damage due to brain cell death.

There are various classification systems for ischemic stroke. The Oxford Community Stroke Project classification (OCSP, also known as the Bamford or Oxford classification) relies primarily on the initial symptoms; based on the extent of the symptoms, the stroke episode is classified as total anterior circulation infarct (TACI), partial anterior circulation infarct (PACI), lacunar infarct (LACI) or posterior circulation infarct (POCI). These four entities predict the extent of the stroke, the area of the brain affected, the underlying cause, and the prognosis.

Whether a subject suffers from stroke, in particular from ischemic stroke, can be determined by well known methods. Moreover, symptoms of stroke are well known in the art and e.g. described in Adams et al. (loc. cit.). E.g., stroke symptoms include sudden numbness or weakness of face, arm or leg, especially on one side of the body, sudden confusion, trouble speaking or understanding, sudden trouble seeing in one or both eyes, and sudden trouble walking, dizziness, loss of balance or coordination.

Further, it is envisaged that the subject in the context of the present invention does not have impaired renal function. Preferably, the subject shall not suffer from renal failure, in particular the subject shall not suffer from acute, chronic and/or end stage renal failure. Further, the subject, preferably, shall not suffer from renal hypertension. How to assess whether a subject exhibits impaired renal function is well known in the art. Renal disorders can be diagnosed by any means known and deemed appropriate. Particularly, renal function can be assessed by means of the glomerular filtration rate (GFR). For example, the GFR may be calculated by the Cockgroft-Gault or the MDRD formula (Levey 1999, Annals of Internal Medicine, 461-470). GFR is the volume of fluid filtered from the renal glomerular capillaries into the Bowman's capsule per unit time. Clinically, this is often used to determine renal function. The GFR was originally estimated (the GFR can never be determined, all calculations derived from formulas such as the Cockgroft Gault formula of the MDRD formula deliver only estimates and not the "real" GFR) by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance (CrCl) is therefore a close approximation of the GFR. The GFR is typically recorded in milliliters per minute (mL/min). The normal range of GFR for males is 97 to 137 mL/min, the normal range of GFR for females is 88 to 128 ml/min. Thus, it is particularly contemplated that the GFR of a subject who does not exhibit impaired renal function is within this range. Moreover, said subject preferably, has a blood creatinine level (in particular a serum creatinine level) of lower than 0.9 mg/dl, more preferably of lower than 1.1 mg/dl and most preferably of lower than 1.3 mg/dl.

Moreover, it is further envisaged that the subject does not suffer from ACS (acute coronary syndrome). The term "ACS" as used herein includes STEMI (ST-elevation myocardial infarction); NSTEMI (non ST-elevation myocardial infarction) and unstable angina pectoris. It is further envisaged that the subject to be tested does not have a history of ACS. In particular, the subject shall not have suffered from ACS within one month prior to carrying out the method of the present invention (to be more precise, within one month prior to obtaining the sample).

It is also contemplated that the subject does not suffer from coronary artery disease. The term "coronary artery disease", abbreviated CAD, frequently also called coronary heart disease (CHD) or atherosclerotic heart disease, is known to the person skilled in the art. Preferably, the term refers to a condition in which the blood vessels that supply blood and oxygen to the heart are narrowed. Coronary artery disease is usually caused by a condition called atherosclerosis, which occurs when fatty material and a substance called plaque builds up on the walls of your arteries. This causes them to get narrow. Particularly, CAD is the result of the accumulation of atheromatous plaques within the walls of the arteries that supply the myocardium (the muscle of the heart). Preferably, a subject who suffers from CAD has at least 50% stenosis (and thus at least 50% occlusion), in at least one major coronary artery. Thus, a subject who does not suffer from CAD, preferably, has less than 50% steonis in the major coronary arteries. How to assess the degree of occlusion of a coronary artery is well known in the art, preferably, the degree is assessed by coronary angiography. While the symptoms and signs of coronary artery disease are noted in the advanced state of disease, most individuals with coronary artery disease show no evidence of disease for decades as the disease progresses before the first onset of symptoms of an acute event, often a "sudden" heart attack, finally arise.

Further, the subject shall not be pregnant. Also, the subject is, preferably, not an athlete.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein. In case, the subject has suffered from paroxysmal atrial fibrillation recently, the sample, preferably, has been obtained at least 30 minutes, and, more preferably, at least three hours, or most preferably, at least 6 hours after termination of the recent paroxysmal atrial fibrillation, i.e. after termination of the episode, in particular, the last episode of paroxysmal atrial fibrillation.

The term "cardiac Troponin" refers to all Troponin isoforms expressed in cells of the heart and, preferably, the subendocardial cells. These isoforms are well characterized in the art as described, e.g., in Anderson 1995, Circulation Research, vol. 76, no. 4:681-686 and Ferrieres 1998, Clinical Chemistry, 44:487-493. Preferably, cardiac Troponin refers to Troponin T and/or Troponin I, and, most preferably, to Troponin T. It is to be understood that isoforms of Troponins may be determined in the method of the present invention together, i.e. simultaneously or sequentially, or individually, i.e. without determining the other isoform at all. Amino acid sequences for human Troponin T and human Troponin I are disclosed in Anderson, loc cit and Ferrieres 1998, Clinical Chemistry, 44:487-493.

The term "cardiac Troponin" encompasses also variants of the aforementioned specific Troponins, i.e., preferably, of Troponin I, and more preferably, of Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific Troponin (in particular over the entire length). Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85:2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. Preferably, the cardiac troponin variants have immunological properties (i.e. epitope composition) comparable to those of human troponin T or troponin I. Thus, the variants shall be recognizable by the aforementioned means or ligands used for determination of the concentration of the cardiac troponins. Thus, the variants shall be recognizable by the aforementioned means or ligands used for determination of the concentration of the cardiac troponins. Such fragments may be, e.g., degradation products of the Troponins. Further included are variants which differ due to posttranslational modifications such as phosphorylation or myristylation. Preferably the biological property of troponin I and its variant is the ability to inhibit actomyosin ATPase or to inhibit angiogenesis in vivo and in vitro, which may e.g. be detected based on the assay described by Moses et al. 1999 PNAS USA 96 (6): 2645-2650). Preferably the biological property of troponin T and its variant is the ability to form a complex with troponin C and I, to bind calcium ions or to bind to tropomyosin, preferably if present as a complex of troponin C, I and T or a complex formed by troponin C, troponin I and a variant of troponin T. It is known that low concentrations of circulating cardiac troponin may be detected in subjects at various conditions, but further studies are required to understand their respective role and rate (Masson et al., Curr Heart Fail Rep (2010) 7:15-21).

Preferably, the cardiac Troponin is Troponin T, in particular human Troponin T. Preferably, the amount of Troponin T is determined by using an high sensitive Troponin assays as described in the Examples, or in WO2012/025355.

As used herein, the term "BNP-type peptides" comprise pre-proBNP, proBNP, NT-proBNP, and BNP. In particular, the BNP-type peptide is NT-proBNP or BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP). Preferably, BNP-type peptides according to the present invention are NT-proBNP, BNP, and variants thereof. BNP is the active hormone and has a shorter half-life than the respective inactive counterpart NT-proBNP. BNP is metabolized in the blood, whereas NT-proBNP circulates in the blood as an intact molecule and as such is eliminated renally. The in-vivo half-life of NTproBNP is 120 min longer than that of BNP, which is 20 min (Smith 2000, J Endocrinol. 167:239-46). Preanalytics are more robust with NT-proBNP allowing easy transportation of the sample to a central laboratory (Mueller 2004, Clin Chem Lab Med 42:942-4). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50:867-73). Therefore, depending on the time-course or properties of interest, either measurement of the active or the inactive forms of the natriuretic peptide can be advantageous. The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NTproBNP referred to in accordance with the present invention further encompasses allelic and other variants of said specific sequence for human NT-proBNP discussed above. Specifically, envisaged are variant polypeptides which are on the amino acid level preferably, at least 50%, 60%, 70%, 80%, 85%, 90%, 92%, 95%, 97%, 98%, or 99% identical to human NT-proBNP, preferably over the entire length of human NT-proBNP. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85:2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of human NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Lab Invest 230:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

CRP, herein also referred to as C-reactive protein, is an acute phase protein that was discovered more than 75 years ago to be a blood protein that binds to the C-polysaccharide of pneumococci. CRP is known as a reactive inflammatory marker and is produced by a distal organ (i.e. the liver) in response or reaction to chemokines or interleukins originating from the primary lesion site. CRP consists of five single subunits, which are non covalently linked and assembled as a cyclic pentamer with a molecular weight of approximately 110-140 kDa. Preferably, CRP as used herein relates to human CRP. The sequence of human CRP is well known and disclosed, e.g., by Woo et al. (J. Biol. Chem. 1985. 260 (24), 13384-13388). The level of CRP is usually low in normal individuals but can rise 100- to 200-fold or higher due to inflammation, infection or injury (Yeh (2004) Circulation. 2004; 109: II-11-II-14). It is known that CRP is an independent factor for the prediction of a cardiovascular risk. Particularly, it has been shown that CRP is suitable as a predictor for myocardial infarction, stroke, peripheral arterial disease and sudden cardiac death. Moreover, elevated CRP amounts may also predict recurrent ischemia and death in subjects with acute coronary syndrome (ACS) and those undergoing coronary intervention. Determination of CRP is recommended by expert panels (e.g. by the American Heart Association) in patients with a risk of coronary heart disease (see also Pearson et al. (2003) Markers of Inflammation and Cardiovascular Disease. Circulation, 107:499-511). The term CRP also relates to variants thereof.

Preferably, the amount of CRP in a sample of a subject is determined by using CRP assays with a high sensitivity. The CRP determined by such assays is frequently also referred to as high sensitivity CRP (hsCRP). hsCRP assays are, e.g., used to predict the risk of heart disease. Suitable hsCRP assays are known in the art. A particularly preferred hsCRP assay in the context of the present invention is the Roche/Hitachi CRP (Latex) HS test with a detection limit of 0.1 mg/l.

Interleukin-6 (abbreviated as IL-6) is an interleukin is secreted by T cells and macrophages to stimulate immune response, e.g. during infection and after trauma, especially burns or other tissue damage leading to inflammation. It acts as both a pro-inflammatory and anti-inflammatory cytokine. In humans, it is encoded by the IL6 gene. The sequence of human IL-6 can be assessed via GenBank (see NM_000600.3 for the polynucleotide sequence, and NP_000591.1 for the amino acid sequence). IL-6 signals through a cell-surface type I cytokine receptor complex consisting of the ligand-binding IL-6Rα chain (CD126), and the signal-transducing component gp130 (also called CD130). CD130 is the common signal transducer for several cytokines including leukemia inhibitory factor (LIF), ciliary neurotropic factor, oncostatin M, IL-11 and cardiotrophin-1, and is almost ubiquitously expressed in most tissues. In contrast, the expression of CD126 is restricted to certain tissues. As IL-6 interacts with its receptor, it triggers the gp130 and IL-6R proteins to form a complex, thus activating the receptor. These complexes bring together the intracellular regions of gp130 to initiate a signal transduction cascade through certain transcription factors, Janus kinases (JAKs) and Signal Transducers and Activators of Transcription.

The marker IGFBP7 (Insulin like growth factor binding protein 7) is well known in the art. The Insulin like growth factor binding protein (IGFBP) system plays an important role in cell growth and differentiation. It comprises two ligands, IGF-I and IGF-II, two receptors, type 1 and type 2 IGF receptors, and as of 1995 six IGF-binding proteins (IGFBPs), IGFBP-1 to -6 (Jones, J. I., et al., Endocr. Rev. 16 (1995) 3-34). Recently the IGFBP family has been expanded to include the IGFBP-related proteins (IGFBP-rPs), which have significant structural similarities with the IGFBPs (Hwa, V., et al., Endocr. Rev 20 (1999) 761-787). Thus, the IGFBP superfamily includes the six conventional IGFBPs, which have high affinity for IGFs, and at least 10 IGFBPrPs, which not only share the conserved amino-terminal domain of the IGFBPs but also show some degree of affinity for IGFs and insulin. The IGFBP-rPs are a group of cysteine-rich proteins that control diverse cellular functions, such as cellular growth, cell adhesion and migration, and synthesis of the extracellular matrix. In addition, these proteins might be involved in biological processes like tissue proliferation and differentiation, reproduction, angiogenesis, wound repair, inflammation, fibrosis, and tumorigenesis (Hwa, V., et al., Endocr. Rev 20 (1999) 761-787).

IGF binding protein 7 (=IGFBP7) is a 30-kDa modular glycoprotein known to be secreted by endothelial cells, vascular smooth muscle cells, fibroblasts, and epithelial cells (Ono, Y., et al., Biochem Biophys Res Comm 202 (1994)

1490-1496). In the literature this molecule has also been denominated as FSTL2; IBP 7; IGF binding protein related protein I; IGFBP 7; IGFBP 7v; IGFBP rPl; IGFBP7; IGFB-PRP1; insulin like growth factor binding protein 7; insulin like growth factor binding protein 7 precursor; MAC25; MAC25 protein; PGI2 stimulating factor; and PSF or Prostacyclin stimulating factor. Northern blot studies revealed a wide expression of this gene in human tissues, including heart, brain, placenta, liver, skeletal muscle, and pancreas (Oh, Y., et al., J. Biol. Chem. 271 (1996) 30322-30325).

IGFBP7 was initially identified as a gene differentially expressed in normal leptomeningeal and mammary epithelial cells, compared with their counterpart tumor cells, and named meningioma-associated cDNA (MAC25) (Burger, A. M., et al., Oncogene 16 (1998) 2459-2467). The expressed protein was independently purified as a tumor derived adhesion factor (later renamed angiomodulin) (Sprenger, C. C., et al., Cancer Res 59 (1999) 2370-2375) and as a prostacyclin stimulating factor (Akaogi, K., et al., Proc Natl Acad Sci USA 93 (1996) 8384-8389). It has additionally been reported as T1A12, a gene down-regulated in breast carcinomas (StCroix, B., et al., Science 289 (2000) 1197-1202).

Preferably, the term "IGFBP7" refers to human IGFBP7. The sequence of the protein is well known in the art and is e.g. accessible via GenBank (NP_001240764.1). IGFBP7 as used herein, preferably, encompasses also variants of the specific IGFBP7 polypeptides.

Preferred markers to be determined in connection with the aformementioned method are cardiac Troponin, a BNP-type peptide, in particular NT-proBNP (N-terminal prohormone of brain natriuretic peptide), and hsCRP, or IL-6 (Interleukin-6).

Determining the amount of a peptide or polypeptide as referred to in the context of the method of the present invention relates to measuring the amount or concentration, preferably, semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay and methods which may utilize labeled molecules in various sandwich, competition, or other assay formats. Such assays are, preferably, based on detection agents such as antibodies which specifically recognize the peptide or polypeptide to be determined. The detection agents shall be either directly or indirectly capable of generating a signal indicating the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical de-vices such as mass-spectrometers, NMR-analyzers, or chromatography devices. Further, methods include micro-plate ELISA-based methods, fully-automated or robotic immuno-assays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Preferably, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand, i.e. the complex of the ligand formed in step (a). According to a preferred embodiment, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound ligand, i.e. the ligand or the ligand/peptide complex, will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F (ab) 2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Further suitable techniques for the determination of a polypeptide or peptide are described in the following.

Binding of a ligand may be measured directly, e.g. by NMR or surface plasmon resonance. Measurement of the binding of a ligand, according to preferred embodiments, is performed by an analyzer unit of a system disclosed herein. Thereafter, an amount of the measured binding may be calculated by a computing device of a system disclosed herein. If the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labeling may be done by direct or indirect methods. Direct labeling involves coupling of the label directly (covalently or noncovalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, avail-able as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suit-able camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include 35S, 1251, 32p, 33P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20 (1): 9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations. According to preferred embodiments of the subject invention, the determination of an "amount" is performed by the disclosed system, whereby a computing device determines the "amount" based on contacting and measuring steps performed by one or more analyzer units of said system.

The term "comparing" as used herein encompasses comparing the amount of a marker as referred to herein, in particular of peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or by a computing device (e.g., of a system disclosed herein). For a computer assisted comparison, the value of the determined amount may be compared to values corresponding to suitable references which are stored in a database by a computer program. The computer program may further evaluate the result of the comparison, i.e. automatically provides the desired assessment in a suitable output format. The said result may, preferably, serve as an aid in assessing whether the subject shall be subjected to an imaging based diagnostic assessment as set forth herein elsewhere, or not. For example, a result of a comparison may be given as raw data (absolute or relative amounts), and in some cases as an indicator in the form of a word, phrase, symbol, or numerical value which may be indicative of a particular diagnosis. Therefore, the reference amount is to be chosen so that either a difference or a similarity in the compared amounts allows for carrying out diagnosis of the present invention.

The term "reference amount" as used herein refers to an amount which allows for allocation of a subject into either the group of subjects who suffered from paroxysmal atrial fibrillation (AF) recently, or into a group of subjects who did not suffer from paroxysmal atrial fibrillation (AF) recently. Such a reference amount can be a threshold amount which separates these groups from each other. Accordingly, the reference amount for a biomarker as referred to herein shall be an amount which allows for allocation of a subject into a group of subjects who suffered from paroxysmal atrial fibrillation (AF) recently, or into a group of subjects who did not suffer from paroxysmal atrial fibrillation (AF) recently. A suitable threshold amount separating the two groups can be calculated without further ado by the statistical tests referred to herein elsewhere based on amounts of the marker as referred to herein from either a subject or group of subjects who suffered from paroxysmal atrial fibrillation (AF) recently, or a subject or group of subjects who did not suffer from paroxysmal atrial fibrillation (AF) recently. Preferred referenced amounts which can be derived from the aforementioned subjects or group of subjects are indicated elsewhere herein.

The reference amount may be used to define and establish a threshold amount. The threshold amount, preferably, allows for a rule-in and/or a rule-out that the subjects suffered from paroxysmal atrial fibrillation (AF) recently. Said rule-in and/or rule-out may be provided by the computing device of a system disclosed herein based on said comparison of the calculated "amount" to a reference or a threshold. For example, a computing device of a system may provide an indicator, in the form of a word, symbol, or numerical value which is indicative of a rule-in or rule-out. The reference amount applicable for an individual subject may vary depending on various physiological parameters such as age, gender, or subpopulation, as well as on the means used for the determination of the polypeptide or peptide referred to herein. A suitable reference amount may be determined from a reference sample to be analyzed together, i.e. simultaneously or subsequently, with the test sample. Preferably, the reference amount is determined by the carrying out the method of the present invention. Preferably, the reference amount is determined in a sample/samples obtained within the same time periods with respect to the recent paroxysmal AF.

Preferably, the reference amount is a calculated reference amount. Preferably, the calculated reference amount shall allow for differentiating between a subject who suffered from paroxysmal atrial fibrillation (AF) recently, and subject who did not suffer from paroxysmal atrial fibrillation (AF) recently. Reference amounts can, in principle, be calculated for a cohort of subjects as specified above based on the average or mean values for a given biomarker by applying standard statistically methods. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity/specificity pairs resulting from continuously varying the decision threshold over the entire range of data observed. The clinical performance of a diagnostic method depends on its accuracy, i.e. its ability to correctly allocate subjects to a certain assessment, prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the aforementioned method of the present invention can be, preferably, a threshold or cut off amount and can be generated, preferably, by establishing a ROC for said cohort as described above and deriving a threshold amount therefrom. Dependent on a desired sensitivity and specificity for a diagnostic method, the ROC plot allows deriving suitable thresholds.

Preferably, the following applies as diagnostic algorithm (in particular if the reference is a calculated reference amount):

Preferably, an increased amount of the at least one marker (increased amounts of the markers) as compared to the reference amount(s) is indicative for the diagnosis of a recent paroxysmal atrial fibrillation, whereas a decreased amount of the at least one at least one marker (decreased amounts of the markers) as compared to the reference amount(s) indicates that the subject did not suffer from paroxysmal atrial fibrillation recently.

Preferred reference amounts are as follows:

With respect to the marker hsCRP, the reference amount is preferably, within a range of 2.5 to 3.5 mg/l, and more preferably, within a range of 3.0 to 3.5 mg/l. Most preferably, the reference amount is 3.0 or 3.5 mg/l.

With respect to the cardiac troponin, the reference amount is preferably, within a range of 4.0 to 6 pg/ml, and more preferably, within a range of 5.0 to 6.0 pg/ml. Most preferably, the reference amount is 5.5 or 6.0 pg/ml.

With respect to the marker Il-6, the reference amount is preferably, within a range of 1.5 to 2.0 pg/ml, and more preferably, within a range of 1.6 to 1.9 pg/ml. Most preferably, the reference amount is 1.7 or 1.9 pg/ml.

With respect to the marker NT-proBNP, the reference amount is preferably, within a range of 100 to 150 pg/ml, and more preferably, within a range of 110 to 130 pg/ml. Most preferably, the reference amount is 125 or 150 pg/ml.

A preferred reference amount for IGFBP7 is within a range from 70 to 100 ng/ml, or more preferably within the range between 70 to 90 ng/ml. A particularly preferred reference amount is 80 ng/ml.

As set forth herein above, the reference amount(s) can be also derived from (i) a subject or group of subjects known to have suffered from a recent paroxysmal atrial fibrillation. In this case, an amount (amounts) of the at least one marker which is (which are) essentially the same amount(s) and/or an increased amount (increased amounts) of the at least one marker in the sample from the subject as compared to the reference amount(s) is (are) indicative for the diagnosis of a recent paroxysmal atrial fibrillation. Preferably, the reference amount(s) is (are) derived from a sample of said subject or from samples of said group or subjects.

Preferably, by applying the aforementioned reference amount it can be ruled in that the subject has suffered from a recent paroxysmal atrial fibrillation.

Additionally or alternatively, the reference amount(s) can be, preferably, derived from (i) a subject or group of subjects known not to have suffered from a recent paroxysmal atrial fibrillation. Preferably, an amount (amounts) of the at least one marker which is (which are) essentially the same amount(s) and/or a decreased amount (increased amounts) of the at least one marker in the sample from the subject as compared to the reference amount(s) indicate(s) that the subject did not suffer from paroxysmal atrial fibrillation. Preferably, the reference amount is derived from a sample of said subject or from samples of said group or subjects.

Preferably, by applying the aforementioned reference amount(s) it can be ruled out that the subject has suffered from a recent paroxysmal atrial fibrillation.

The definition of the term "subject" is given elsewhere herein. The definitions also apply to the reference subject(s). Preferably, the subject to be tested and the reference subject(s) have the same age, gender and/or race. Accordingly, it is preferred that the reference amount is adjusted for age, gender and/or race.

The markers as referred to herein can be determined alone. However, they may be determined together, i.e. the method of the present invention may encompass the determination of one markers, two markers, three markers, or four markers. A particular preferred combination is the determination of a cardiac Troponin and of CRP (i.e. hsCRP). The combined determination of these markers, preferably, allows for diagnosing whether the subject has suffered from paroxysmal atrial fibrillation, or not, within a period of 30 days before the sample has been obtained, and more preferably, within a period of one week before the sample has been obtained.

A further preferred combination is the determination of a cardiac Troponin and of a BNP-type peptide, in particular NT-proBNP. The combined determination of these markers, in particular, allows for diagnosing whether the subject has suffered from paroxysmal atrial fibrillation, or not, within a period of one week before the sample has been obtained.

A further preferred combination is the determination of a cardiac Troponin and of IL-6. The combined determination of these markers, preferably, allows for diagnosing whether the subject has suffered from paroxysmal atrial fibrillation, or not, within a period of 30 days before the sample has been obtained, and more preferably, within a period of one week before the sample has been obtained.

Another preferred combination is the determination of IL-6 and of a BNP-type peptide, in particular NT-proBNP. The combined determination of these markers, in particular, allows for diagnosing whether the subject has suffered from paroxysmal atrial fibrillation, or not, within a period of one week before the sample has been obtained.

Another preferred combination is the determination of CRP and of a BNP-type peptide, in particular NT-proBNP. The combined determination of these markers, in particular, allows for diagnosing whether the subject has suffered from paroxysmal atrial fibrillation, or not, within a period of one week before the sample has been obtained.

A further preferred combination is the determination of hsCRP and of IL-6. The combined determination of these markers, preferably, allows for diagnosing whether the subject has suffered from paroxysmal atrial fibrillation, or not, within a period of 30 days before the sample has been obtained, and more preferably, within a period of one week before the sample has been obtained.

In an aspect of the invention, a method for establishing an aid for diagnosing a recent paroxysmal atrial fibrillation in a subject, is contemplated, said method comprising:

a) determining the amount of at least one marker selected from the group consisting of a cardiac Troponin, a BNP-type peptide, hsCRP (high sensitive CRP), IL-6 (Interleukin-6) and IGFBP7 (Insulin like growth factor binding protein 7) by (i) bringing the sample into contact with a detection agent (detection agents) that specifically bind(s) to said at least one marker for a time sufficient to allow for the formation of a complex(es) of the said detection agent(s) and the at least one marker from the sample, (ii) measuring the amount(s) of the formed complex(es), wherein the said amount(s) of the formed complex(es) are proportional to the amount(s) of the at least one marker present in the sample, and (iii) transforming the amount(s) of the formed complex into an amount (amounts) of the at least one marker reflecting the amount(s) of the at least one marker present in the sample;

b) comparing said amount(s) to a reference (references); and c) establishing an aid for diagnosing a recent paroxysmal atrial fibrillation in a subject based on the result of the comparison made in step b).

In another aspect of the invention, a system for establishing an aid for diagnosing a recent paroxysmal atrial fibrillation in a subject, comprising:

a) an analyzer unit configured to bringing the sample into contact with a detection agent (or detection agents) that specifically bind(s) to said at least one marker selected from the group consisting of a cardiac Troponin, a BNP-type peptide, hsCRP (high sensitive CRP), IL-6 (Interleukin-6) and IGFBP7 (Insulin like growth factor binding protein 7) for a time sufficient to allow for the formation of a complex of the said detection agent and the at least one marker from the sample, b) an analyzer unit configured to measure the amount of the formed complex, wherein the said amount of the formed complex is proportional to the amount of the at least one marker present in the sample, c) a computing device having a processor and in operable communication with said analysis units, and d) a non-transient machine readable media including a plurality of instructions executable by the processor, the instructions, when executed transform the amount of the formed complex into an amount of the at least one marker reflecting the amount of the at least one marker present in the sample, compare said amount to a reference, and establish an aid for diagnosing a recent paroxysmal atrial fibrillation in a subject based on the result of said comparison to said reference.

A suitable detection agent may be, in an aspect, an antibody, in particular a monoclonal antibody) which specifically binds to the at least one marker, i.e. a detection agent which binds to a cardiac Troponin, a BNP-type peptide, hsCRP (high sensitive CRP), or to IL-6 (Interleukin-6), in a sample of a subject to be investigated by the method of the invention. Another detection agent that can be applied, in an aspect, may be an aptamere which specifically binds to the at least one marker in the sample. In yet an aspect the, sample is removed from the complex formed between the detection agent and the at least one marker prior to the measurement of the amount of formed complex. Accordingly, in an aspect, the detection agent may be immobilized on a solid support. In yet an aspect, the sample can be removed from the formed complex on the solid support by applying a washing solution. The formed complex shall be proportional to the amount of the at least one marker present in the sample. It will be understood that the specificity and/or sensitivity of the detection agent to be applied defines the degree of proportion of at least one marker comprised in the sample which is capable of being specifically bound. Further details on how the determination can be carried out are also found elsewhere herein. The amount of formed complex shall be transformed into an amount of at least one marker reflecting the amount indeed present in the sample. Such an amount, in an aspect, may be essentially the amount present in the sample or may be, in another aspect, an amount which is a certain proportion thereof due to the relationship between the formed complex and the amount present in the original sample.

In yet an aspect of the aforementioned method, step a) may be carried out by an analyzer unit, in an aspect, an analyzer unit as defined elsewhere herein.

In an aspect of the method of the invention, the amount(s) determined in step a) is (are) compared to a reference. In an aspect, the reference is a reference as defined elsewhere herein. In yet another aspect, the reference takes into account the proportional relationship between the measured amount of complex and the amount present in the original sample. Thus, the references applied in an aspect of the method of the invention are artificial references which are adopted to reflect the limitations of the detection agent that has been used. In another aspect, said relationship can be also taken into account when carrying out the comparison, e.g., by including a normalization and/or correction calculation step for the determined amount prior to actually comparing the value of the determined amount and the reference. Again, the normalization and/or correction calculation step for the determined amount adopts the comparison step such that the limitations of the detection agent that has been used are reflected properly. In an aspect, the comparison is carried out automatically, e.g., assisted by a computer system or the like.

The aid for diagnosing a recent paroxysmal atrial fibrillation is established based on the comparison carried out in step b) by allocating the subject either into a group of subjects having suffered from paroxysmal atrial fibrillation recently or into a group of subject not having suffered from paroxysmal atrial fibrillation recently as set forth herein elsewhere. As discussed elsewhere herein already, the allocation of the investigated subject must not be correct in 100% of the investigated cases. Moreover, the groups of subjects into which the investigated subject is allocated are artificial groups in that they are established based on statistical considerations, i.e. a certain preselected degree of likelihood based on which the method of the invention shall operate. In an aspect of the invention, the aid for optimizing a risk assessment is established automatically, e.g., assisted by a computing device or the like, as described and disclosed herein.

In an aspect of the method of the invention, said method further comprises a step of recommending anticoagulation therapy according to the comparison results. Preferably, anticoagulation therapy is recommended if the subject has suffered from paroxysmal atrial fibrillation recently.

In an aspect of the aforementioned method, steps b) and/or c) are carried out by one or more analyzer units as set forth elsewhere herein.

The definitions and explanations given herein above apply mutatis mutandis to the following:

Method for Identifying a Subject Who is Treatable with Anticoagulation Therapy

Moreover, the present invention also relates to method for identifying a subject who is treatable with anticoagulation therapy:

(a) determining the amount of at least one marker selected from the group consisting of a cardiac Troponin, NT-proBNP (N-terminal prohormone of brain natriuretic peptide), hsCRP, IL-6 (Interleukin-6) and IGFBP7 (Insulin like growth factor binding protein 7) in a sample from a subject who is suspected to have suffered from paroxysmal atrial fibrillation recently, and (b) comparing the, thus, determined amount(s) of said at least one marker to a reference amount (to reference amounts), whereby a subject is identified who is treatable to anticoagulation therapy, wherein the subject does not suffer from atrial fibrillation at the time at which the sample is obtained.

Preferably, a subject being treatable with anticoagulation therapy is identified by carrying out the further step of c) identifying a subject who is treatable with anticoagulation therapy, based on the results of the comparison carried out in step b).

In an embodiment, the determination of the amount(s) of the biomarker(s) in step (a) is done by contacting the sample with a detection agent that specifically binds to the biomarker (or with detection agents that specifically bind to the biomarkers), thereby forming an complex with the detection agent and the biomarker, detecting the amount(s) of the complex(es) formed, thereby determining the amount of the biomarker. The term "detection agent" has been specified elsewhere herein.

The term "treatable with" as used herein means that the subject is likely to benefit from treatment with the therapy, either through prevention of a condition or by effecting an improvement in said condition.

The term "identifying" as used herein means assessing whether a subject will be susceptible for anticoagulation therapy or not, and, thus, requires said therapy or not. Preferably, a subject is treatable with said therapy, if the subject will benefit from said therapy. In particular, a subject benefits from said therapy, it the therapy reduces the risk of stroke of said subject. Moreover, for a subject who is treatable with a said therapy the advantages of said therapy shall outweigh the disadvantages (particularly disadvantages caused by adverse side effect of a certain treatment regimen, but also with respect to the costs). Also, for a subject who is not treatable with said therapy, the disadvantages (particularly, with respect to adverse side effects but also with respect to the costs due to an over-treatment) of said therapy will outweigh the advantages. Particularly, if a subject does not require a certain cardiac therapy, costs that would result from on overtreatment will be saved and/or adverse side effects can be avoided. As will be understood by those skilled in the art, such an assessment is usually not intended to be correct for all (i.e., 100%) of the subjects to be identified. The term, however, requires that a statistically significant portion of subjects can be identified (e.g., a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

Preferred markers to be determined in connection with the aformementioned method are cardiac Troponin, a BNP-type peptide, in particular NT-proBNP (N-terminal prohormone of brain natriuretic peptide), and hsCRP, or IL-6 (Interleukin-6).

Anticoagulation therapies are well known in the art. As used herein, the term, preferably, relates to a therapy which aims to reduce or prevent coagulation of blood. A preferred anticoagulation therapy is administration of an anticoagulant. A preferred anticoagulant is selected from the group consisting of heparin, a coumarin derivative, such as warfarin or dicumarol, tissue factor pathway inhibitor (TFPI), antithrombin III, factor IXa inhibitors, factor Xa inhibitors, inhibitors of factors Va and VIIIa, thrombin inhibitors.

A subject who is treatable with anticoagulation therapy may be also treatable with a treatment with at least one antiarrhythmic agent. Preferred antiarrhythmic agent are Class I agents such as Quinidine and Lidocaine, class II agents, i.e. beta blockers, class III agents such as Ibutilide, class IV agents such as Verapamil, or class V agents such as Digoxin.

The term "reference amount" has been explained elsewhere herein. In the context of the aforementioned method, the term refers to an amount which allows for allocation of a subject into either the group of subjects being treatable with anticoagulation therapy, or into a group of subjects not being treatable with anticoagulation therapy. Such a reference amount can be a threshold amount which separates these groups from each other. A suitable threshold amount separating the two groups can be calculated without further ado by the statistical tests referred to herein elsewhere based on amounts of the marker as referred to herein from either a subject or group of subjects who suffered from paroxysmal atrial fibrillation (AF) recently, or a subject or group of subjects who did not suffer from paroxysmal atrial fibrillation (AF) recently.

Preferably, the following applies as diagnostic algorithm (in particular if the reference is a calculated reference amount):

Preferably, an increased amount of the at least one marker (increased amounts of the markers) as compared to the reference amount(s) is indicative for a subject who is treatable with anticoagulation therapy, whereas a decreased amount of the at least one at least one marker (decreased amounts of the markers) as compared to the reference amount(s) is indicative for a subject not being treatable with anticoagulation therapy.

Further, the reference amount(s) can be derived from (i) a subject or group of subjects known to be treatable with anticoagulation therapy. In this case, an amount (amounts) of the at least one marker which is (which are) essentially the same amount(s) and/or an increased amount (increased amounts) of the at least one marker in the sample from the subject as compared to the reference amount(s) is (are) indicative for a subject being treatable with anticoagulation therapy. Preferably, the reference amount(s) is (are) derived from a sample of said subject or from samples of said group or subjects.

Preferably, by applying the aforementioned reference amount it can be ruled in that the subject is treatable with anticoagulation therapy.

Additionally or alternatively, the reference amount(s) can be, preferably, derived from (i) a subject or group of subjects known not to be treatable with anticoagulation therapy. Preferably, an amount (amounts) of the at least one marker which is (which are) essentially the same amount(s) and/or a decreased amount (increased amounts) of the at least one marker in the sample from the subject as compared to the reference amount(s) indicate(s) that the subject is not treatable with anticoagulation therapy. Preferably, the reference amount is derived from a sample of said subject or from samples of said group or subjects.

Preferably, by applying the aforementioned reference amount(s) it can be ruled out that the subject is not treatable with anticoagulation therapy.

Moreover, the present invention envisages a method of treating a patient with anticoagulation therapy and/or with an antiarrhythmic agent, the method comprising:

(a) determining the amount of at least one marker selected from the group consisting of a cardiac Troponin, NT-proBNP (N-terminal prohormone of brain natriuretic peptide), hsCRP, IL-6 (Interleukin-6) and IGFBP7 (Insulin like growth factor binding protein 7) in a sample from a subject who is suspected to have suffered from paroxysmal atrial fibrillation recently, and (b) comparing the, thus, determined amount(s) of said at least one marker to a reference amount (to reference amounts), and (c) selecting and/or initiating an anticoagulation therapy and/or with an antiarrhythmic agent when the amount(s) of the at least on marker is above the reference amount (are above the reference amounts).

The method referred to above, may further comprise step (b1) identifying a subject as to have suffered from atrial fibrillation recently when the amount of the at least one marker (or the amounts) is above the reference amount (are above the reference amounts).

The present invention also relates to the use of i) at least one marker selected from the group consisting of at least one marker selected from the group consisting of a cardiac Troponin, a BNP-type peptide, hsCRP (high sensitive CRP), IL-6 (Interleukin-6) and IGFBP7 (Insulin like growth factor binding protein 7) or ii) of a detection agent which specifically binds to a BNP-type peptide, and/or of a detection agent which specifically binds to a cardiac Troponin, and/or of a detection agent which specifically binds to hsCRP, and/or of a detection agent which specifically binds to IL-6, and/or of a detection agent which specifically binds to IGFBP7, in a sample of a subject for diagnosing a recent paroxysmal atrial fibrillation in the subject. Preferably, the subject does not suffer from atrial fibrillation at the time at which the sample is obtained The present invention also relates to the use of i) at least one marker selected from the group consisting of at least one marker selected from the group consisting of a cardiac Troponin, a BNP-type peptide, hsCRP (high sensitive CRP), IL-6 (Interleukin-6) and IGFBP7 (Insulin like growth factor binding protein 7) or ii) of a detection agent which specifically binds to a BNP-type peptide, and/or of a detection agent which specifically binds to a cardiac Troponin, and/or of a detection agent which specifically binds to hsCRP, and/or of a detection agent which specifically binds to IL-6, and/or of a detection agent which specifically binds to IGFBP7, in a sample of a subject for identifying a subject who is treatable with anticoagulation therapy. Preferably, the subject does not suffer from atrial fibrillation at the time at which the sample is obtained The present invention also relates to the use of i) at least one marker selected from the group consisting of at least one marker selected from the group consisting of a cardiac Troponin, a BNP-type peptide, hsCRP (high sensitive CRP), IL-6 (Interleukin-6) and IGFBP7 (Insulin like growth factor binding protein 7) or ii) of a detection agent which specifically binds to a BNP-type peptide, and/or of a detection agent which specifically binds to a cardiac Troponin, and/or of a detection agent which specifically binds to hsCRP, and/or of a detection agent which specifically binds to IL-6, and/or of a detection agent which specifically binds to IGFBP7, for the manufacture of a diagnostic composition for diagnosing in a subject a recent paroxysmal atrial fibrillation. Preferably, the subject does not suffer from atrial fibrillation at the time at which the sample is obtained The present invention also relates to the use of i) at least one marker selected from the group consisting of at least one marker selected from the group consisting of a cardiac Troponin, a BNP-type peptide, hsCRP (high sensitive CRP), IL-6 (Interleukin-6) and IGFBP7 (Insulin like growth factor binding protein 7) or ii) of a detection agent which specifically binds to a BNP-type peptide, and/or of a detection agent which specifically binds to a cardiac Troponin, and/or of a detection agent which specifically binds to hsCRP, and/or of a detection agent which specifically binds to IL-6, and/or of a detection agent which specifically binds to IGFBP7 for the manufacture of a diagnostic composition for identifying a subject who is treatable with anticoagulation therapy. Preferably, the subject does not suffer from atrial fibrillation at the time at which the sample is obtained.

The term "detection agent" as used herein refers to an agent that is capable of specifically recognizing and binding to the biomarker polypeptide(s) present in a sample. Moreover, the said agent shall allow for direct or indirect detection of the complex formed by the said agent and the biomarker. Direct detection can be achieved by including into the agent a detectable label. Indirect labelling may be achieved by a further agent that specifically binds to the complex comprising the biomarker and the detection agent wherein the said further agent is than capable of generating a detectable signal. Suitable compounds which can be used as detection agents are well known in the art. Preferably, the detection agent is an antibody or aptamere which specifically binds to the biomarker. The term "antibody" has been described elsewhere herein.

The present invention also relates to an anticoagulant or an antiarrhythmic agent for treating a subject who has suffered from a recent paroxysmal atrial fibrillation, wherein the subject is treated when the amount of at least one marker selected from the group consisting of a cardiac Troponin, a BNP-type peptide, hsCRP (high sensitive CRP), IL-6 (Interleukin-6) and IGFBP7 (Insulin like growth factor binding protein 7) in a sample from the patient larger than the reference amount.

According to a preferred embodiment of the present invention, a device adapted for diagnosing a recent paroxysmal atrial fibrillation is provided comprising a) an analyzer unit comprising a detection agent (or agents) which specifically binds to a marker selected from the group consisting of a cardiac Troponin, a BNP-type peptide, hsCRP, IL-6 (Interleukin-6) and IGFBP7 (Insulin like growth factor binding protein 7), said unit being adapted for determining the amount(s) of the marker(s) in a sample; and b) an analyzer unit for comparing the determined amount(s) with reference amount(s), whereby a recent paroxysmal atrial fibrillation is diagnosed, said unit comprising a database with a reference amount (or amounts) as set forth herein elsewhere and a computer-implemented algorithm carrying out the comparison as set forth herein elsewhere.

According to another preferred embodiment of the present invention, a device adapted for identifying a subject who is treatable with anticoagulation therapy is provided comprising a) an analyzer unit comprising a detection agent (or agents) which specifically binds to a marker selected from the group consisting of a cardiac Troponin, a BNP-type peptide, hsCRP, IL-6 (Interleukin-6) and IGFBP7 (Insulin like growth factor binding protein 7), said unit being adapted for determining the amount(s) of the marker(s) in a sample; and b) an analyzer unit for comparing the determined amount(s) with reference amount(s), whereby a subject is identified who is treatable with anticoagulation therapy, said unit comprising a database with a reference amount (or amounts) as set forth herein elsewhere and a computer-implemented algorithm carrying out the comparison as set forth herein elsewhere.

Preferred reference amounts and algorithms are disclosed elsewhere herein.

The term "device" as used herein relates to a system comprising the aforementioned units operatively linked to each other as to allow the diagnosis or monitoring according to the methods of the invention. Preferred detection agents which can be used for the analysing unit are disclosed elsewhere herein. The analysing unit, preferably, comprises said detection agents in immobilized form on a solid support which is to be contacted to the sample comprising the biomarkers the amount of which is to be determined. Moreover, the analysing unit can also comprise a detector which determines the amount of detection agent which is specifically bound to the biomarker(s). The determined amount can be transmitted to the evaluation unit. Said evaluation unit comprises a data processing element, such as a computer, with an implemented algorithm for carrying out a comparison between the determined amount and a suitable reference. Suitable references are either derived from a subject or group of subjects as defined above in context with the method of the present invention. The results may be given as output of parametric diagnostic raw data, preferably, as absolute or relative amounts. It is to be understood that these data will need interpretation by the clinician. However, also envisage are expert system devices wherein the output comprises processed diagnostic raw data the interpretation of which does not require a specialized clinician.

A preferred embodiment of the instant disclosure includes a system for diagnosing a recent paroxysmal atrial fibrillation. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system may include one or more analyzer units utilized for practicing the subject disclosure. The analyzer units of the system disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electro-magnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the amount of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined amount of one or more markers disclosed herein, and a suitable reference, is embodied and performed by executing the instructions. The results may be given as output of parametric diagnostic raw data or as absolute or relative amounts. According to various embodiments of the system disclosed herein, a "diagnosis" may be provided by the computing device of a system disclosed herein based on said comparison of the calculated "amount" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

Finally, the invention pertains to a kit adapted for carrying out a method of the present invention comprising a detection agent which specifically binds to a marker selected from the group consisting of a brain natriuretic peptide, a cardiac troponin, and sFlt-1, reference standards as well as instructions for carrying out the said method.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Further, the kit shall comprise at least one standard for a reference as defined herein above, i.e. a solution with a predefined amount for the at least one marker representing a reference amount. Such a standard may represent, e.g., the amount of the at least one marker from a subject or group of subjects having suffered from a paroxysmal atrial fibrillation recently or a subject or group of subjects not having suffered from a paroxysmal atrial fibrillation recently.

In some embodiments, a kit disclosed herein includes at least one component or a packaged combination of components for practicing a disclosed method. By “packaged combination” it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of “packaged combination.” In some embodiments, the kits include at least one probe, for example an antibody (having specific affinity for an epitope of a biomarker as disclosed herein. For example, the kits may include an antibody that is labelled with a fluorophore or an antibody that is a member of a fusion protein. In the kit, the probe may be immobilized, and may be immobilized in a specific conformation. For example, an immobilized probe may be provided in a kit to specifically bind target protein, to detect target protein in a sample, and/or to remove target protein from a sample.

According to some embodiments, kits include at least one probe, which may be immobilized, in at least one container. Kits may also include multiple probes, optionally immobilized, in one or more containers. For example, the multiple probes may be present in a single container or in separate containers, for example, wherein each container contains a single probe.

In some embodiments, a kit may include one or more non-immobilized probe and one or more solid support that does or does not include an immobilized probe. Some such embodiments may comprise some or all of the reagents and supplies needed for immobilizing one or more probes to the solid support, or some or all of the reagents and supplies needed for binding of immobilized probes to specific proteins within a sample.

In certain embodiments, a single probe (including multiple copies of the same probe) may be immobilized on a single solid support and provided in a single container. In other embodiments, two or more probes, each specific for a different target protein or a different form of a single target protein (such as a specific epitope), a provided in a single container. In some such embodiments, an immobilized probe may be provided in multiple different containers (e.g., in single-use form), or multiple immobilized probes may be provided in multiple different containers. In further embodiments, the probes may be immobilized on multiple different type of solid supports. Any combination of immobilized probe(s) and container(s) is contemplated for the kits disclosed herein, and any combination thereof may be selected to achieve a suitable kit for a desired use.

A container of the kits may be any container that is suitable for packaging and/or containing one or more components disclosed herein, including for example probes (for example, an antibody), controls, buffers, and reagents (for example, conjugate and/or substrate). Suitable materials include, but are not limited to, glass, plastic, cardboard or other paper product, wood, metal, and any alloy thereof. In some embodiments, the container may completely encase an immobilized probe(s) or may simply cover the probe to minimize contamination by dust, oils, etc., and expose to light. In some further embodiments, he kits may comprise a single container or multiple containers, and where multiple containers are present, each container may be the same as all other containers, different than others, or different than some but not all other containers.

Method for Diagnosing Ongoing Atrial Fibrillation in a Subject

Advantageously, it has been found in the context of the studies underlying the present invention that the determination of IGFBP7 in a sample from a subject allows for diagnosing whether a subject suffers from an ongoing atrial fibrillation, or not.

Accordingly, the present invention relates to a method for diagnosing atrial fibrillation in a subject, comprising (a) determining the amount of the biomarker IGFBP7 in a sample from the subject, and (b) comparing the amount of the biomarker IGFBP7 as determined in step (a) to a reference amount.

Preferably, an amount of the biomarker IGFBP7 in the sample from the subject above the reference amount indicates that the subject has atrial fibrillation. Also preferably, an amount of the biomarker IGFBP7 in the sample from the subject below the reference amount indicates that the subject has not atrial fibrillation.

In an embodiment, the determination of the amount of the biomarker in step (a) is done by contacting the sample with a detection agent that specifically binds to the biomarker, thereby forming an complex with the detection agent and the biomarker, detecting the amount of the complex formed, thereby determining the amount of the biomarker IGFBP7. The term “detection agent” has been specified elsewhere herein. In an embodiment, the agent is an antibody such as a monoclonal antibody which specifically binds to IGFBP7.

The term “detecting” a biomarker as used herein refers to methods of detecting the quantity of the biomarker in the sample employing appropriate methods of detection described elsewhere herein.

In an embodiment, the aforementioned method may further comprise the step (c) of providing a diagnosis of atrial fibrillation when the amount of the biomarker in the sample from the subject is above the reference amount and/or of providing a diagnosis of the absence of atrial fibrillation when the amount of the biomarker in the sample from the subject is below the reference amount.

In the context of the aforementioned method of diagnosing atrial fibrillation, it shall be diagnosed whether the subject suffers from atrial fibrillation at the time point at which the sample to be tested has been obtained. Thus, in contrast to the method of diagnosing a recent atrial fibrillation, it shall be diagnosed whether the subject suffers from an ongoing atrial fibrillation, or not. The term “atrial fibrillation” has been defined above. In the context of the aforementioned method, the atrial fibrillation may be permanent, persistent or, in particular, paroxysmal atrial fibrillation.

The term “diagnosing atrial fibrillation” as used in connection with the aforementioned method is used to indicate that the method according to the present invention will classify an individual as having atrial fibrillation or in the alternative as not having atrial fibrillation. An amount of biomarker IGFBP7 above the reference amount is used for providing a diagnosis of atrial fibrillation.

The term “indicates that the subject has atrial fibrillation” in the context of the aforementioned method is used to illustrate that an amount of IGFBP7 above the reference amount is very valuable but is not diagnostic without error. Not in all (100%) of the patients with atrial fibrillation the amount of the biomarker above the reference amount and not in all healthy individuals the level of the biomarker is below the reference level. As the skilled artisan will appreciate, in many diseases, no biochemical marker has 100% specificity and at the same time 100% sensitivity. In such case assessment e.g., with regard to the level of biomarker IGFBP7 in atrial fibrillation is performed with a certain likelihood, e.g. at a given level of specificity or at a given level of sensitivity. The skilled artisan is fully familiar with the mathematical/statistical methods used to calculate specificity, sensitivity, positive predictive value, negative predictive value, reference value or total error. Any of these parameters can be calculated and used to obtain an indication of the presence or absence of atrial fibrillation.

The phrase "providing a diagnosis" as used herein in connection with the aforementioned refers to using the information or data generated relating to the level or presence of IGFBP7 in a sample of a patient to diagnose atrial fibrillation in the patient. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of IGFBP7 to a reference level. In In some embodiments, the information or data includes an indication that the patient is diagnosed with atrial fibrillation.

The term "subject" as used in connection with the aforementioned method relates to animals, preferably mammals, and, more preferably, humans. The subject may be male (in particular a male being older than 60 or 65 years). Further, the subject may be female (in particular a female being older than 60 or 65 years).

The subject in accordance with the aforementioned method of diagnosing atrial fibrillation shall be suspected to suffer from paroxysmal atrial fibrillation. A subject suspected to suffer from paroxysmal atrial fibrillation, preferably, is a subject who has one or more risk factors of atrial fibrillation. These risk factors are well known in the art and include heart disease, including valve problems and a history of heart attack and heart surgery, systemic hypertension, especially if it's not well controlled with lifestyle changes or medications, and alcohol consumption. Preferably, the subject being suspected to belongs to a risk group. In particular, it is envisaged that the subject is a subject with proven or suspected cardiac disorders including subjects having risk factors predisposing to cardiac disorders such as arterial or systemic hypertension, diabetes mellitus, smokers, individuals with hyperlipemia or signs of the metabolic syndrome, in particular if the subject is at advanced age (more than 60, 65, 70 and preferably more than 75, or 80 years of age). Alternatively, or additionally the subject may, preferably, suffer from valvular disorders, preferably from mitral valve disorders.

In an embodiment, the method of the present invention the subject suffers from hypertension and/or from heart failure. The terms "hypertension" and "heart failure" were defined above. The definitions apply accordingly. In a preferred embodiment, the subject suffers from heart failure classified as heart failure stage A or stage B according to the ACC/AHA classification (as referred to above). In a particular preferred embodiment of the present invention, the subject to be tested is classified as stage A subject (according to the ACC/AHA classification as referred to above).

In an embodiment of the method of diagnosing (an ongoing) atrial fibrillation, the subject preferably does not have a known history of atrial fibrillation. Accordingly, the subject shall not have been diagnosed to suffer from atrial fibrillation previously, in particular by conventional means.

The term "sample" has been defined above. In an embodiment, the sample is a blood, serum or plasma sample.

In contrast to the method of diagnosing a recent paroxysmal atrial fibrillation, it is envisaged that the atrial fibrillation occurs in connection with stroke. Thus, the subject to be tested may suffer from stroke at the time point at which the sample is obtained or may have a history of stroke. Preferably, a subject who has a history of stroke has suffered from stroke within three months before the sample to be tested has been obtained. More preferably, a subject who has history of stroke has suffer from stroke within one months for the sample has been obtained.

A definition for the marker IGFBP7 (Insulin like growth factor binding protein 7) has been given above.

How to determine the amount of a biomarker has been described in connection of the method of diagnosing a recent paroxysmal atrial fibrillation. The amount of IGFBP7 can be determined accordingly.

The term "reference amount" in connection with the aforementioned method refers to a predetermined value. In this context "amount" encompasses the absolute amount, the relative amount or concentration as well as any value or parameter which correlates thereto or can be derived therefrom. As the skilled artisan will appreciate the reference amount is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference amount meeting those requirements. In one embodiment the reference amount is determined in reference samples from healthy individuals. The reference amount in one embodiment has been predetermined in reference samples from the disease entity to which the patient belongs. In certain embodiments the reference amount can e.g. be set to any percentage between 25% and 75% of the overall distribution of the values in a disease entity investigated. In other embodiments the reference amount can e.g. be set to the median, tertiles or quartiles as determined from the overall distribution of the values in reference samples from a disease entity investigated. In one embodiment the reference amount is set to the median value as determined from the overall distribution of the values in a disease entity investigated. The reference amount may vary depending on various physiological parameters such as age, gender or subpopulation, as well as on the means used for the determination of the IGFBP7 referred to herein. In one embodiment, the reference sample is from essentially the same type of cells, tissue, organ or body fluid source as the sample from the individual or patient subjected to the method of the invention, e.g. if according to the invention blood is used as a sample to determine the amount of IGFBP7 in the individual, the reference amount is also determined in blood or a part thereof.

In an embodiment, the reference amount is a (predetermined) amount which allows for differentiating between a subject who suffers from atrial fibrillation and a subject who does not suffer from atrial fibrillation.

A preferred reference amount for IGFBP7 is within a range from 70 to 115 ng/ml, or more preferably in the range between 80 to 90 ng/ml. A particularly preferred reference amount is 90 ng/ml.

In certain embodiments, the term "above the reference level" refers to a level of the biomarker in the sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in biomarker level in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample.

In certain embodiments, the term "decrease" or "below" herein refers to a level of the biomarker in the sample from the individual or patient below the reference level or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference level. In certain embodiments, the term decrease in biomarker level in the sample from the individual or patient wherein the decreased level is at most about 0.9-, 0.8-, 0.7-, 0.6-, 0.5-, 0.4-, 0.3-, 0.2-, 0.1-, 0.05-, or 0.01-fold of the reference level, e.g. predetermined from a reference sample, or lower.

In a preferred embodiment of the aforementioned method, the further comprises the determination of the amount of a BNP-type peptide, and the comparison of the thus determined amount to a reference amount (for said BNP-type peptide).

Accordingly, the present invention also provides a method for diagnosing atrial fibrillation in a subject, comprising (a) determining the amount of IGFBP7 and a BNP-type peptide in a sample from the subject, and
(b) comparing the amounts as determined in step (a) to reference amounts (i.e. to a reference amount for IGFBP7 and to a reference amount for said BNP-type peptide).

Preferably, an amount of the biomarker IGFBP7 in the sample from the subject above the reference amount and an amount of said BNP-type peptide above the reference amount indicates that the subject has atrial fibrillation. Also preferably, an amount of the biomarker IGFBP7 in the sample from the subject below the reference amount and an amount of the BNP-type peptide in the sample from the subject below the reference amount indicates that the subject does not have atrial fibrillation.

In accordance with this method, a preferred reference amount for NT-proBNP is within a range from 200 to 500 ng/l, or more preferably in the range between 300 to 400 ng/1. A particularly preferred reference amount is 400 ng/1.

The term "BNP-type peptide" has been defined above. The definition applies accordingly. In an embodiment, the BNP-type peptide is NT-proBNP.

In a preferred embodiment of the aforementioned method, the method further comprises the step of recommending a therapy suitable for the treatment of atrial fibrillation. Said therapy may comprise any treatment known in the art which is used for the therapy of ongoing atrial fibrillation. Preferably, said therapy intends to (i) terminate said atrial fibrillation such as electrical cardioversion or cardioversion with an antiarrhythmic agent or to (ii) anticoagulation therapy.

The term "anticoagulation therapy" has been defined above. Preferred antiarrhythmic agents are also described above.

Moreover, the present invention envisages a method of treating a patient with a therapy suitable for the treatment of atrial fibrillation, the method comprising:

(a) determining the amount of IGFBP7 and, optionally, of a BNP-type peptide in a sample from the subject, and
(b) comparing the amount (or the amounts) as determined in step (a) to a reference amount (or to reference amounts), and
(c) selecting and/or initiating a therapy suitable for the treatment of atrial fibrillation when the amount of IGFBP7 (or the amounts of IGFBP7 and the BNP-type peptide) is above the reference amount (are above the reference amounts).

The method referred to above, may further comprise step (b1) of identifying a subject as to suffer from atrial fibrillation when the amount the amount of IGFBP7 (or the amounts of IGFBP7 and the BNP-type peptide) is above the reference amount (are above the reference amounts).

The present invention further relates to the use of i) IGFBP7 and, optionally, a BNP-type peptide or ii) of a detection agent which specifically binds to IGFBP and, optionally, of a detection agent which specifically binds to a BNP-type peptide in a sample of a subject for diagnosing atrial fibrillation, in particular an ongoing atrial fibrillation, in said subject.

The present invention further relates to the use of i) IGFBP7 and, optionally, a BNP-type peptide or of ii) a detection agent which specifically binds to IGFBP7 and, optionally, of a detection agent which specifically binds to a BNP-type peptide for the manufacture of a diagnostic composition for diagnosing atrial fibrillation. Preferably, an amount of the biomarker IGFBP7 in the sample from the subject above the reference amount (and, optionally, an amount of said BNP-type peptide above the reference amount) indicates that the subject has atrial fibrillation. Also preferably, an amount of the biomarker IGFBP7 in the sample from the subject below the reference amount (and, optionally, an amount of the BNP-type peptide in the sample from the subject below the reference amount) indicates that the subject does not have atrial fibrillation.

According to a preferred embodiment of the present invention, a device adapted for diagnosing ongoing atrial fibrillation is provided comprising (a) an analyzer unit comprising a detection agent which specifically binds to IGFBP (and optionally a detection agent which specifically binds to a BNP-type peptide), said unit being adapted for determining the amount(s) of the marker(s) in a sample; and
(b) an analyzer unit for comparing the determined amount (s) with reference amount(s), whereby an ongoing atrial fibrillation is diagnosed, said unit comprising a database with a reference amount (reference amounts) and a computer-implemented algorithm carrying out the comparison as set forth herein elsewhere.

The term "device" has been defined elsewhere herein. The term "detection agent" has been specified elsewhere herein. In an embodiment, the agent is an antibody such as a monoclonal antibody which specifically binds to the marker (i.e. IGFBP and the BNP-type peptide, respectively).

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1: Patient Cohort

TnT-hs, IL-6, NT-proBNP, and hsCRP levels have been determined in plasma samples of n=46 patients with blood sampled and biomarkers assayed, in sinus rhythm (SR) at 12-month visit. All patients have >=1 recurrence of Atrial fibrillation from randomization to 12-month visit. All 46 patients spontaneously converted to sinus rhythm.

0-7 days after paroxysmal Atrial fibrillation (AF); n=9 patients 8-30 days after paroxysmal AF; n=10 patients Example 2: Assays Troponin T was determined using Roche's electrochemiluminescence ELISA sandwich test Elecsys Troponin T hs (high sensitive) STAT (Short Turn Around Time) assay. The test employs two monoclonal antibodies specifically directed against human cardiac troponin T. The antibodies recognize two epitopes (amino acid position 125-131 and 136-147) located in the central part of the cardiac troponin T protein, which consists of 288 amino acids. The hs-TnT assay allows a measurement of troponin T levels in the range of 3 to 10000 pg/mL.

NT-proBNP was determined using Roche's electrochemiluminescence ELISA sandwich test Elecsys proBNP II STAT (Short Turn Around Time) assay. The test employs two monoclonal antibodies which recognize epitopes located in the N-terminal part (1-76) of proBNP (1-108).

IL-6 (Interleukin 6) was measured by an electrochemiluminescent immunoassay (ECLIA, Roche Diagnostics). The test was performed using a Cobas E601 analyzer from Roche Diagnostics. The test is based on a first incubation with a biotinylated monoclonal IL-6-specific antibody and a second incubation with a monoclonal IL-6-specific antibody labeled with a ruthenium complex and streptavidin-coated microparticles.

High-sensitive (hs) CRP was determined using a particle enhance immunoturbidimetric assay from Roche Diagnostics (Tina-quant Cardiac C-reactive Protein (Latex) High Sensitive). In this test, Anti-CRP antibodies coupled to latex microparticles react with antigen in the sample to form an antigen/antibody complex. Following agglutination, the complex is measured turbidimetrically.

Example 3: Results

The results are shown in the following table.

| days after paroxysmal atrial fibrillation | hsTnT (pg/mL) | Nt-proBNP | hsCRP mg/l | IL-6 pg/ml |
|---|---|---|---|---|
| 0-7 (n = 6) | 8.37 | 191 | 4.20 | 2.21 |
| 8-30 (n = 10) | 6.51 | 58 | 4.35 | 2.04 |

Data evaluation showed that patients with TnT-hs levels (independent from other biomarker) above a reference value (in the study >6 pg/mL) are suspected to have paroxysmal Atrial fibrillation and may benefit from anticoagulation. It is even shown, that TnT-hs levels may be detected in patients presenting 7-30 days later in sinus rhythm. Other markers such as hsCRP show a slightly different kinetic after spontaneous termination of atrial fibrillation and may thus individually and/or in combination assist in the detection of past episodes of paroxysmal atrial fibrillation.

Thus, the diagnosis of recent occurrence of paroxysmal Atrial Fibrillation in patients presenting within 7-30 days later in sinus rhythm may be achieved with detection of enhanced levels of Troponin T alone or in combination with a marker of inflammation (CRPhs, IL6) and/or a marker of heart failure (NT-proBNP).

Example 4: Determination of IGFBP7 and NT-proBNP in Subject with Ongoing Atrial Fibrillation IGFBP7 was determined in plasma samples from 49 apparently healthy elderly subjects. Of these 49 subjects, 17 presented with an episode of AF detected by ECG at clinical visit. NT-proBNP was determined in plasma samples from 139 apparently healthy elderly subjects. Of these 139 subjects, 45 presented with an episode of AF detected by ECG at clinical visit. 28/82 controls matched for sex and age presented without an episode of AF on ECG.

NT-proBNP has been determined as described above. For detection of IGFBP7 in human samples, a sandwich ELISA was used. For capture and detection of the antigen, aliquots of an anti-IGFBP7 polyclonal antibody from R&D Systems (Catalogue number: AF 1334) was conjugated with biotin and digoxigenin, respectively.

The results are shown in the following table:

| | Ongoing atrial fibrillation at ECG | | | | |
|---|---|---|---|---|---|
| | YES | | NO | | |
| Marker | N | Median [Q1-Q3] | N | Median [Q1-Q3] | p* |
| NT-proBNP (ng/L) | 58 | 582 [192-1014] | 81 | 165 [90-371] | 0.0004 |
| IGFBP7 (ng/ml) | 17 | 90 [65-116] | 28 | 66.5 [61-86.5] | 0.0271 |

*P adjusted for sex and age

Biomarker levels were compared in subjects, who presented or not with an episode of AF detected by ECG. As it can be derived from the table, NT-proBNP and IGFBP7 were found significantly higher in subjects with an ongoing AF.

Example 5: Individual Cases

A 71 year old female patient with class A heart failure has a BMI below 30 kg/m$^2$ and hypertension. The patient has no history of stroke. The patient presents in sinus rhythm. Troponin T, Interleukin 6 and Nt-ProBNP are determined in a plasma sample obtained from the patient. The Troponin T value is below 6 pg/ml, the Interleukin 6 value is below 1.5 pg/ml and the Nt-ProBNP value is below 125 pg/ml. Data evaluation is indicative, that the patient has had no recent episodes of paroxysmal Atrial fibrillation in the last week.

A 69 year old male patient with class A heart failure has a BMI below 30 kg/m$^2$ and hypertension. The patient presents in sinus rhythm. Troponin T, C Reactive Protein and Nt-ProBNP are determined in a plasma sample obtained from the patient. The Troponin T value is below 6 pg/ml, the C Reactive Protein value is between 1 and 3 mg/l and the Nt-ProBNP value is below 125 pg/ml. Data evaluation is indicative, that the patient has had no past episodes of paroxysmal fibrillation up to 7-30 days before. The patient is informed to return to a follow up visit in 12 months or if symptoms worsen. After 12 months the patient comes to a follow up visit. Troponin T, C Reactive Protein and Nt-ProBNP are determined in a plasma sample obtained from the patient. The Troponin T value is above 6 pg/ml, the C Reactive Protein value is above 3 mg/l and the Nt-ProBNP value is above 125 pg/ml. Data evaluation is indicative, that the patient has had past episodes of paroxysmal fibrillation up to 7-30 days before and may benefit from anticoagulation.

An 68 year old male patient with class B heart failure has a BMI above 30 $kg/m^2$ and hypertension. The patient presents in sinus rhythm. Troponin T, C Reactive Protein and Nt-ProBNP are determined in a plasma sample obtained from the patient. The Troponin T value is above 6 pg/ml, the CRP value is above 3 mg/l and the Nt-ProBNP value is above 125 pg/ml. Increased amounts of the markers) as compared to the reference amount(s) indicate that the subject suffers from past episodes of paroxysmal atrial fibrillation up to 7-30 days ago. This example demonstrates that determination of Troponin T alone or in combination with further markers is suited to detect patients that may benefit from anticoagulation because of diagnosis of paroxysmal atrial fibrillation.

A 76 year old female patient with class A heart failure has no history of atrial fibrillation. The patient presents in sinus rhythm. Troponin T, Interleukin 6, Nt-ProBNP and IGFBP-7 are determined in a plasma sample obtained from the patient. The Troponin T value is above 6 pg/ml, the Interleukin 6 value is above 1.5 pg/ml, the Nt-ProBNP value is above 125 pg/ml and the IGFBP-7 value is above 80 ng/ml. Data evaluation is indicative, that the patient has had recent episodes of paroxysmal Atrial fibrillation in the last few days and may benefit from preventive therapy.

SUMMARY

The data of the study underlying the present invention indicate that cardiac Troponins can be a useful marker to diagnose the occurrence of a recent paroxysmal atrial fibrillation. TnT-hs is a soluble biomarker that is released from the heart into the blood stream during atrial fibrillation and the data show that it is detectable for several days, before it declines after arrhythmia dating back about one week. A similar pattern is shown for hsCRP, NT-proBNP and IL-6 and thus, these markers may alone or in combination assist in the detection of paroxysmal atrial fibrillation of up to one month after spontaneous termination of atrial fibrillation.

The invention claimed is:

1. A method for diagnosing a recent paroxysmal atrial fibrillation in a subject, comprising:

(a) detecting the amounts of NT-proBNP and cardiac Troponin T in a sample from the subject, and (b) comparing the detected amounts of said NT-proBNP and cardiac Troponin T to reference amounts, whereby a subject who has suffered from a recent paroxysmal atrial fibrillation is identified, wherein the subject does not suffer from atrial fibrillation at the time at which the sample is obtained, and (c) administering an anticoagulation therapy to the subject diagnosed as having a recent paroxysmal atrial fibrillation, wherein the recent atrial fibrillation terminated spontaneously, wherein the recent paroxysmal atrial fibrillation occurred within 30 days before the sample has been obtained, wherein in step (b), amounts of the NT-proBNP and cardiac Troponin T which are the same as or higher than reference amounts derived from a subject or group of subjects known to have suffered from a recent paroxysmal atrial fibrillation are indicative for the diagnosis of a recent paroxysmal atrial fibrillation.

2. The method of claim 1, wherein the recent paroxysmal atrial fibrillation did not occur in connection with a stroke.

3. The method of claim 1, wherein the sample is a blood, serum or plasma sample.

4. The method claim 1, wherein the subject is human.

5. The method of claim 1, wherein:

(i) an amount of cardiac Troponin T which is the same as or higher than the reference amount for cardiac Troponin T is indicative for the diagnosis that the subject has suffered from paroxysmal atrial fibrillation within a period of 30 days before the sample has been obtained, (ii) an amount of cardiac Troponin T which is the same as or higher than the reference amount for cardiac Troponin T and an amount of NTproBNP which is the same as or higher than the reference amount for NT-proBNP are indicative for the diagnosis that the subject has suffered from paroxysmal atrial fibrillation within a period of 7 days before the sample has been obtained, and (iii) an amount of cardiac Troponin T which is the same as or higher than the reference amount for cardiac Troponin T and an amount of NT-proBNP which is lower than the reference amount for NTproBNP are indicative for the diagnosis that the subject has suffered from paroxysmal atrial fibrillation within a period of 8 to 30 days before the sample has been obtained.

6. The method of claim 1, wherein the detecting step further comprises detecting the amount of IGFBP7.

7. The method of claim 1, wherein the anticoagulation therapy is selected from the group consisting of heparin, a coumarin derivative, tissue factor pathway inhibitor (TFPI), antithrombin III, factor IXa inhibitors, factor Xa inhibitors, inhibitors of factors Va and VIIIa, thrombin inhibitors.

8. The method of claim 1, wherein the recent paroxysmal atrial fibrillation occurred within 1 to 7 days before the sample has been obtained.

9. The method of claim 2, wherein the subject does not have a history of stroke.

10. A method for diagnosing and treating a paroxysmal atrial fibrillation in a subject, said method comprising:

(a) detecting an amount of N-terminal prohormone of brain natriuretic peptide (NTproBNP) and an amount of cardiac Troponin T, and optionally an amount of at least one other marker selected from the group consisting of hsCRP (high sensitive C-reactive protein), IL-6 (Interleukin-6) and IGFBP7 (Insulin like growth factor binding protein 7) in a plasma sample from the subject, (b) comparing the detected amounts to reference amounts, whereby a subject who has suffered from an episode of paroxysmal atrial fibrillation is identified, (c) administering an anticoagulant or an antiarrhythmic agent to the subject identified as having suffered from an episode of paroxysmal atrial fibrillation, wherein a) the subject does not suffer from atrial fibrillation at the time at which the sample is obtained; b) the subject is suspected to have suffered from the episode of paroxysmal atrial fibrillation; c) the episode of atrial fibrillation occurred within 30 days before the sample is obtained; and d) the episode of atrial fibrillation terminated spontaneously, wherein in step (b), amounts which are the same as or higher than reference amounts derived from a subject or group of subjects known to have suffered from a recent paroxysmal atrial fibrillation are indicative for the diagnosis of a recent paroxysmal atrial fibrillation.

11. The method of claim 5, wherein an amount of cardiac Troponin T which is the same as or higher than the reference amount for cardiac Troponin T and an amount of NTproBNP which is lower than the reference amount for NT-proBNP are indicative for the diagnosis that the subject has suffered from paroxysmal atrial fibrillation within a period of 8 to 30 days before the sample has been obtained.

* * * * *